US011229447B2

(12) United States Patent
Mazhar et al.

(10) Patent No.: US 11,229,447 B2
(45) Date of Patent: Jan. 25, 2022

(54) SYSTEMS, INSTRUMENTS AND METHODS FOR TREATING SINUSES

(71) Applicant: EXCELENT LLC, Raleigh, NC (US)

(72) Inventors: Kashif Mazhar, Raleigh, NC (US); Arlynn Celeste Baker, Matthews, NC (US); Sean Christopher Biette, Cary, NC (US); Tiffany Mae Branch, Marion, NC (US); Tyler Daniel Zaroff, Kannapolis, NC (US); Martin Lyn Tanaka, Cullowhee, NC (US)

(73) Assignee: EXCELENT LLC, Raleigh, NC (US)

( * ) Notice: Subject to any disclaimer, the term of this patent is extended or adjusted under 35 U.S.C. 154(b) by 315 days.

(21) Appl. No.: 16/387,674

(22) Filed: Apr. 18, 2019

(65) Prior Publication Data

US 2019/0328412 A1  Oct. 31, 2019

Related U.S. Application Data

(60) Provisional application No. 62/662,565, filed on Apr. 25, 2018.

(51) Int. Cl.
*A61B 17/24* (2006.01)
*A61B 1/07* (2006.01)
(Continued)

(52) U.S. Cl.
CPC ............. *A61B 17/24* (2013.01); *A61B 1/07* (2013.01); *A61M 3/0283* (2013.01); *A61M 29/02* (2013.01); *A61B 2017/0042* (2013.01); *A61B 2017/246* (2013.01); *A61B 2217/005* (2013.01); *A61B 2217/007* (2013.01); *A61M 2210/0618* (2013.01)

(58) Field of Classification Search
CPC ..... A61B 1/233; A61B 1/0661; A61B 1/0669; A61B 1/0684; A61B 1/015; A61B 1/018; A61B 17/24; A61B 2017/246; A61B 1/05
See application file for complete search history.

(56) References Cited

U.S. PATENT DOCUMENTS 7,361,168 B2   4/2008  Makower et al.
7,520,876 B2   4/2009  Ressemann et al.
(Continued)

FOREIGN PATENT DOCUMENTS

CN   106110430 A   11/2016
CN   106178167 A   12/2016

OTHER PUBLICATIONS

Notification of Transmittal of the International Search Report and the Written Opinion of the International Searching Authority, or the Declaration, in corresponding PCT Application No. PCT/US2019/028455 (dated Sep. 23, 2019).

*Primary Examiner* — Anu Ramana
(74) *Attorney, Agent, or Firm* — Myers Bigel, P.A.

(57) ABSTRACT

An instrument system for treating a sinus of a subject includes an instrument including a base configured to be gripped by an operator, and an elongate probe including a probe proximal end coupled with the base and extending to a probe distal end. The probe includes an aspiration lumen terminating at an inlet port proximate the probe distal end, and a delivery lumen terminating at an outlet port proximate the probe distal end. The instrument also includes a waveguide on the probe and having a light emitting end proximate the probe distal end.

21 Claims, 25 Drawing Sheets

(51) Int. Cl.
*A61M 3/02* (2006.01)
*A61M 29/02* (2006.01)
*A61B 17/00* (2006.01)

(56) References Cited

U.S. PATENT DOCUMENTS

| | | |
|---|---|---|
| 7,678,099 B2 | 3/2010 | Ressemann et al. |
| 7,717,933 B2 | 5/2010 | Becker |
| 8,277,478 B2 | 10/2012 | Drontle et al. |
| 8,414,473 B2 | 4/2013 | Jenkins et al. |
| 8,852,143 B2 * | 10/2014 | Chang .................. A61B 5/065 604/73 |
| 9,089,258 B2 * | 7/2015 | Goldfarb .................. A61B 1/01 |
| 9,101,739 B2 | 8/2015 | Lesch, Jr. et al. |
| 2007/0073269 A1 | 3/2007 | Becker |
| 2007/0249896 A1 | 10/2007 | Goldfarb et al. |
| 2008/0097295 A1 | 4/2008 | Makower et al. |
| 2008/0125626 A1 | 5/2008 | Chang et al. |
| 2008/0172033 A1 | 7/2008 | Keith et al. |
| 2008/0195041 A1 | 8/2008 | Goldfarb et al. |
| 2010/0042046 A1 | 2/2010 | Chang et al. |
| 2010/0211007 A1 | 8/2010 | Lesch, Jr. et al. |
| 2014/0180328 A1 | 6/2014 | Vaccaro et al. |
| 2015/0327945 A1 | 11/2015 | Schaeffer et al. |
| 2016/0008017 A1 | 1/2016 | Makower et al. |
| 2016/0106960 A1 | 4/2016 | Vaccaro et al. |

\* cited by examiner

SYSTEMS, INSTRUMENTS AND METHODS FOR TREATING SINUSES

RELATED APPLICATION(S)

The present application claims the benefit of and priority from U.S. Provisional Patent Application No. 62/662,565, filed Apr. 25, 2018, the disclosure of which is incorporated herein by reference in its entirety.

BACKGROUND OF THE INVENTION

With reference to FIG. 12A, the human nasal cavity is divided vertically by a wall of cartilage called the nasal septum 201. On each side of the nasal septum is a nostril 202 through which the nasal cavity can be accessed. Opposite the septum on each lateral side of the nasal cavity are a series of turbinates (also called concha) comprising of inferior 203, middle 204 and superior turbinate (not shown in any figures) as one goes backwards from the nostrils through the nasal cavity towards the throat. The turbinates are bony ridges that protrude into the nasal cavity.

With reference to FIG. 13A, the paranasal sinuses are a grouping of four pairs of air-filled cavities named after the facial bones in which they are located. The maxillary sinuses 205 are lateral to the nasal cavity in the region of the cheeks, the frontal sinuses 206 are in the forehead region above the eyes, the ethmoid sinuses 207 are located between the two eyes, and sphenoid sinuses 208 are located in the skull base under the pituitary gland. The ethmoid sinuses 207 are separated by a structure called the basal lamina into anterior and posterior ethmoid sinuses. The paranasal sinuses are lined by respiratory epithelium that secrete about a liter of sinus secretions everyday which drains out of the sinus cavity through small orifices called ostia and through the drainage pathways or outflow tract opening into the nasal cavity. The drainage pathway includes the ostia as well as a transition space in the region of the ostia called the "recess". A transition space in the proximity of the frontal sinus is called a frontal recess 209, and a transition space in proximity of the sphenoid sinus and posterior ethmoid sinuses is called spheno-ethmoid recess (not shown in any figures), while the transition space in proximity to maxillary sinus is called the ethmoidal infundibulum 210. The maxillary, anterior ethmoids and frontal sinuses drain into the nasal cavity from under the middle turbinate 204. The posterior ethmoid and sphenoid sinuses drain through the outflow tract called spheno-ethmoid recess, which is located behind the superior turbinate. Efficient and effective transport of secreted mucus is essential for the health of the respiratory epithelial lining of the sinus cavity.

Inflammation of the mucosal linings of the sinus cavity is called sinusitis (or rhinosinusitis) and can be caused by multitude of causes such as anatomical abnormality, allergies, bacteria, or viruses that result in mild to severe symptomatic inflammation of the sino-nasal mucosa of one or more of the four paired sinus cavities (i.e., maxillary, ethmoid, frontal and sphenoid). This results in either the sinuses or their drainage pathways becoming either obstructed or compromised. Symptoms of sinusitis may include nasal obstruction, facial pressure/congestion/fullness, discolored nasal discharge and hyposmia.

Sinusitis is classified as acute sinusitis if less than four weeks in duration or as chronic sinusitis if lasting more than 12 weeks with or without acute exacerbation. Acute sinusitis is usually treated with medical management that includes oral antibiotics, oral antihistamine, topical or oral steroids. If non-responsive to medical management chronic sinusitis may need surgical intervention.

Balloon sinuplasty or balloon dilation of the sinus ostia and drainage pathways have been used to treat patients with chronic sinusitis. Balloon dilation generally involves an endoscopic, catheter-based inflatable balloon located at the distal end of the catheter to enlarge the affected sinus ostia or drainage pathways. Generally, the inflatable balloon is inserted into the constricted ostia or drainage pathways in a deflated state. Once correctly located and inflated, the balloon widens the walls of the sinus ostia or pathways without significant mucosal damage, resulting in lower operative morbidity and pain associated with the procedure for the patient.

Exemplary devices and methods particularly suited for the dilation of anatomic structures associated with maxillary and anterior ethmoid sinuses are disclosed, for example, in U.S. Pat. No. 7,520,876 and U.S. Patent Application Publication No. 2008/0172033. Other systems have also been described for dilating the frontal sinus. For instance, U.S. Patent Application Publication No. 2008/0097295 discloses a frontal sinus guide catheter (FIG. 6B) and a method of treating the frontal sinuses (e.g., FIGS. 8B-8C). U.S. Patent Application Publication No. 2008/0125626 discloses another guide device (e.g., FIGS. 10C and 10C') for transnasal access to the frontal sinuses for treatment.

Existing balloon sinus dilation systems have several drawbacks. Some require multiple steps and multiple instruments. Some available sinus dilation systems require as many as eighteen steps to complete a sinus dilation procedure. Some sinus dilation systems need to be connected to an external light source for trans-illumination while others need to be connected to an image guidance system and hence need additional systems to be able to function.

SUMMARY OF THE INVENTION

According to some embodiments of the invention, an instrument system for treating a sinus of a subject includes an instrument including a base configured to be gripped by an operator, and an elongate probe including a probe proximal end coupled with the base and extending to a probe distal end. The probe includes an aspiration lumen terminating at an inlet port proximate the probe distal end, and a delivery lumen terminating at an outlet port proximate the probe distal end. The instrument also includes a waveguide on the probe and having a light emitting end proximate the probe distal end.

In some embodiments, the instrument system is configured to: execute an aspiration operation wherein the instrument system draws material into the aspiration lumen through the inlet port; execute a fluid delivery operation wherein the instrument system flows a fluid through the delivery lumen and out through the outlet port; and execute an illumination operation wherein the instrument system transmits light through the waveguide and out through the light emitting end.

According to some embodiments, the instrument system is configured to enable the operator to execute the aspiration operation, the fluid delivery operation, and the illumination operation simultaneously.

In some embodiments, the instrument system is configured to enable the operator to execute the aspiration operation and the fluid delivery operation simultaneously.

According to some embodiments, the instrument includes a dilation balloon mounted on the probe proximate the probe distal end, and the instrument system is configured to execute a dilation operation wherein the dilation balloon is expanded.

In some embodiments, the instrument system is configured to enable the operator to execute the dilation operation simultaneously with at least one of the aspiration operation and the fluid delivery operation.

According to some embodiments, the instrument system is configured to enable the operator to execute the dilation operation, the aspiration operation, and the fluid delivery operation simultaneously.

In some embodiments, the instrument system is configured such that: the probe defines a probe longitudinal axis from the probe proximal end to the probe distal end; the base includes a handle configured to be gripped by a hand of the operator; and the handle has a handle axis extending at a transverse angle to the probe longitudinal axis.

According to further embodiments of the invention, an instrument system for treating a sinus of a subject includes an instrument including a base configured to be gripped by an operator, and an elongate probe including a probe proximal end coupled with the base and extending to a probe distal end. The probe includes an aspiration lumen terminating at an inlet port proximate the probe distal end, and a delivery lumen terminating at an outlet port proximate the probe distal end. The instrument further includes a dilation balloon mounted on the probe proximate the probe distal end.

In some embodiments, the instrument system is configured to: execute an aspiration operation wherein the instrument system draws material into the aspiration lumen through the inlet port; execute a fluid delivery operation wherein the instrument system flows a fluid through the delivery lumen and out through the outlet port; and execute a dilation operation wherein the dilation balloon is expanded.

According to some embodiments, the instrument system is configured to enable the operator to execute the aspiration operation and the fluid delivery operation simultaneously.

In some embodiments, the instrument system is configured to enable the operator to execute the dilation operation simultaneously with at least one of the aspiration operation and the fluid delivery operation.

In some embodiments, the instrument system is configured to enable the operator to execute the dilation operation, the aspiration operation, and the fluid delivery operation simultaneously.

According to some embodiments, the instrument system includes: a rigid, elongate shaft, wherein the aspiration lumen is defined in shaft; and a delivery conduit extending through the aspiration lumen, wherein the delivery lumen is defined in delivery conduit. The dilation balloon is mounted on a distal end of the shaft.

The instrument system may include a supply of a medication fluidly connected to the delivery conduit.

According to method embodiments of the invention, a method for treating a sinus of a subject includes providing an instrument including: a base configured to be gripped by an operator; and an elongate probe including a probe proximal end coupled with the base and extending to a probe distal end. The probe includes: an aspiration lumen terminating at an inlet port proximate the probe distal end; and a delivery lumen terminating at an outlet port proximate the probe distal end. The instrument also includes a waveguide on the probe and having a light emitting end proximate the probe distal end. The method further includes: executing an aspiration operation wherein the instrument system draws material into the aspiration lumen through the inlet port; executing a fluid delivery operation wherein the instrument system flows a fluid through the delivery lumen and out through the outlet port; and executing an illumination operation wherein the instrument system transmits light through the waveguide and out through the light emitting end.

In some embodiments, the method includes executing the aspiration operation, the fluid delivery operation, and the illumination operation simultaneously.

According to method embodiments of the invention, a method for treating a sinus of a subject includes providing an instrument including: a base configured to be gripped by an operator; and an elongate probe including a probe proximal end coupled with the base and extending to a probe distal end. The probe includes: an aspiration lumen terminating at an inlet port proximate the probe distal end; and a delivery lumen terminating at an outlet port proximate the probe distal end. The instrument also includes a dilation balloon mounted on the probe proximate the probe distal end. The method further includes: executing an aspiration operation wherein the instrument system draws material into the aspiration lumen through the inlet port; executing a fluid delivery operation wherein the instrument system flows a fluid through the delivery lumen and out through the outlet port; and executing a dilation operation wherein the dilation balloon is expanded.

In some embodiments, the method includes executing the aspiration operation and the fluid delivery operation simultaneously.

According to some embodiments, the method includes executing the dilation operation simultaneously with at least one of the step of executing the aspiration operation and the step of executing the fluid delivery operation.

In some embodiments, the method includes executing the dilation operation, the aspiration operation, and the fluid delivery operation simultaneously.

DETAILED DESCRIPTION OF EMBODIMENTS OF THE INVENTION

Figure 1:
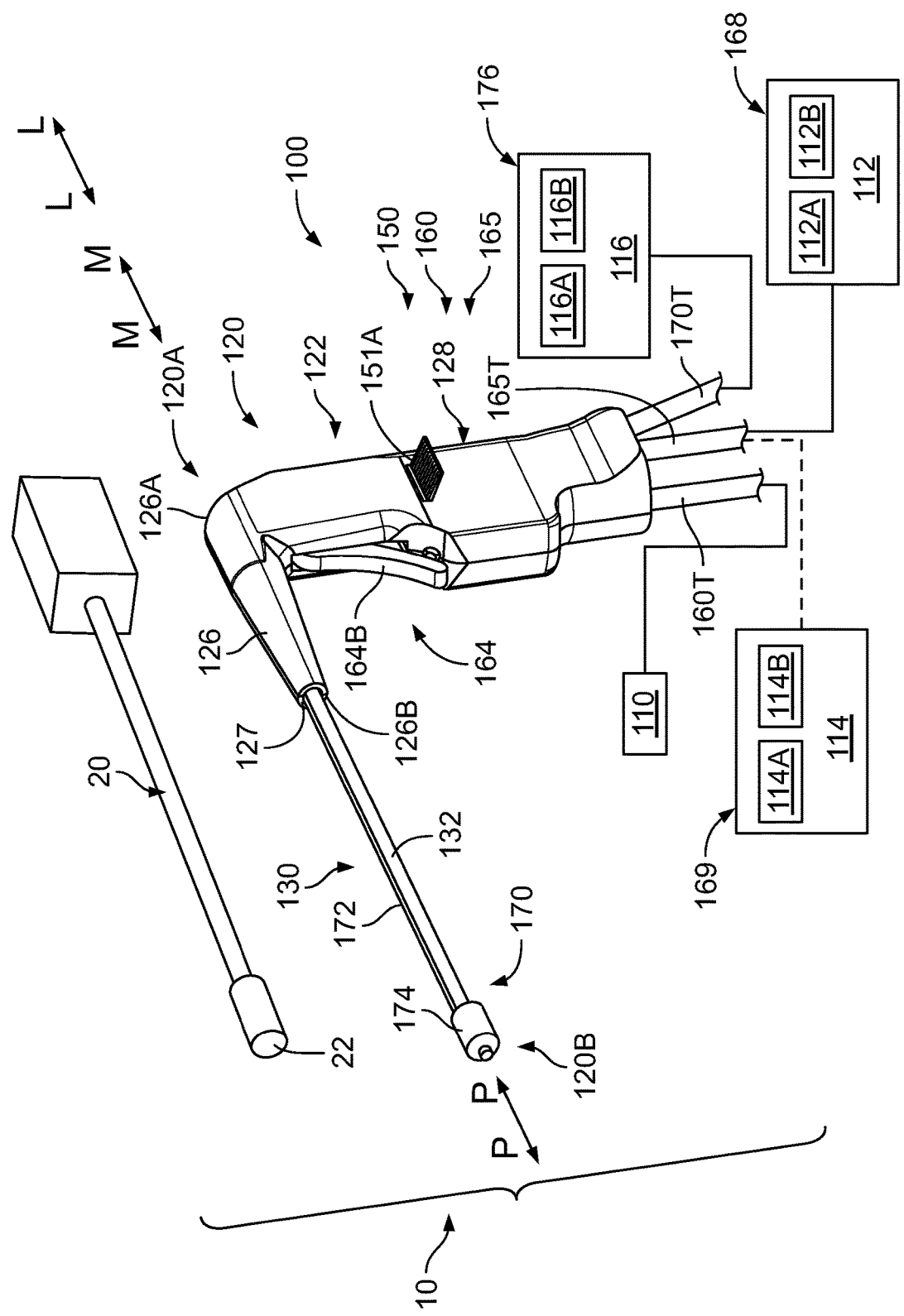
FIG. 1 is front perspective, schematic view of a sinus treatment system according to some embodiments.
Figure 2:
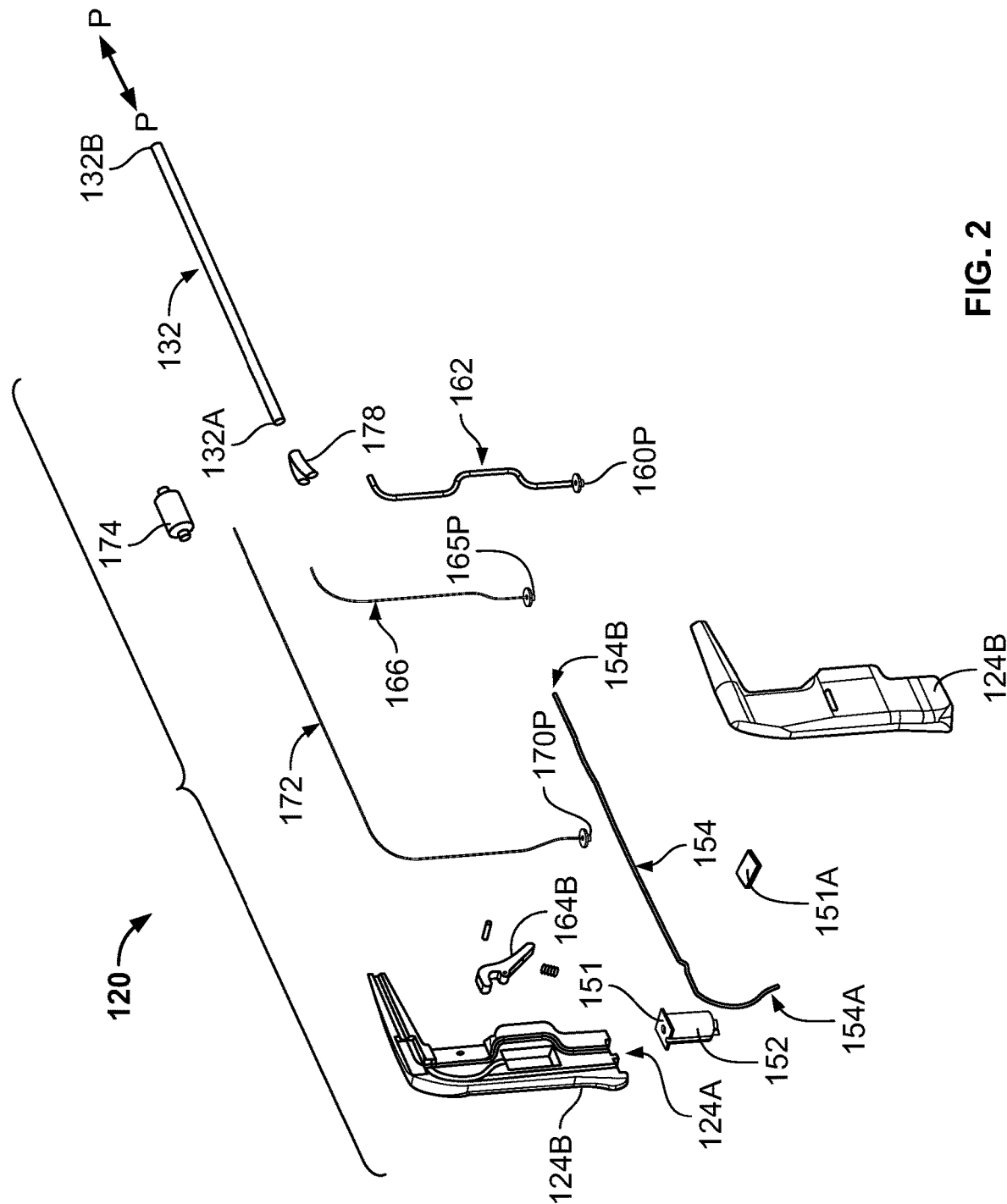
FIG. 2 is an exploded, rear perspective view of an instrument forming a part of the sinus treatment system of FIG. 1.

The present invention now will be described more fully hereinafter with reference to the accompanying drawings, in which illustrative embodiments of the invention are shown. In the drawings, the relative sizes of regions or features may be exaggerated for clarity. This invention may, however, be embodied in many different forms and should not be construed as limited to the embodiments set forth herein; rather, these embodiments are provided so that this disclosure will be thorough and complete, and will fully convey the scope of the invention to those skilled in the art.

It will be understood that when an element is referred to as being "coupled" or "connected" to another element, it can be directly coupled or connected to the other element or intervening elements may also be present. In contrast, when an element is referred to as being "directly coupled" or "directly connected" to another element, there are no intervening elements present. Like numbers refer to like elements throughout.

In addition, spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly.

Well-known functions or constructions may not be described in detail for brevity and/or clarity.

As used herein the expression "and/or" includes any and all combinations of one or more of the associated listed items.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

"Treat," "treating" or "treatment of" (and grammatical variations thereof) as used herein refer to any type of treatment that imparts a benefit to a subject and may mean that the severity of a subject's disease, disorder, or condition is reduced, at least partially improved or ameliorated and/or that some alleviation, mitigation or decrease in at least one clinical symptom associated with the disease, disorder, or condition is achieved and/or there is a delay in the progression of the symptom. In some embodiments, the severity of a disease, disorder, or condition associated with a sinus in a subject may be reduced in the subject compared to the severity of the symptom in the absence of a system and/or method of the present invention.

In some embodiments, a therapeutic as described herein may be administered in a treatment effective amount. A "treatment effective amount" as used herein is an amount that is sufficient to treat (as defined herein) a subject. Those skilled in the art will appreciate that the therapeutic effect(s) need not be complete or curative, as long as some benefit is provided to the subject. In some embodiments, a treatment effective amount may be achieved by administering to a subject a medication as described herein, optionally in an irrigation fluid I, a supply 114B of medication N, and/or an inflation fluid E using a system and/or method of the present invention.

The terms "prevent," "preventing" and "prevention" (and grammatical variations thereof) refer to avoidance, reduction and/or delay of the onset of a symptom associated with a disease, disorder, or condition and/or a reduction in the severity of the onset of a symptom associated with disease, disorder, or condition relative to what would occur in the absence of a system and/or method of the present invention. The prevention can be complete, e.g., the total absence of the symptom. The prevention can also be partial, such that the occurrence of the symptom in the subject and/or the severity of onset is less than what would occur in the absence of a system and/or method of the present invention.

In some embodiments, a therapeutic as described herein may be administered in a prevention effective amount. A "prevention effective amount" as used herein is an amount that is sufficient to prevent (as defined herein) a disease, disorder, or condition and/or a symptom thereof in a subject. Those skilled in the art will appreciate that the level of prevention need not be complete, as long as some benefit is provided to the subject. In some embodiments, a prevention effective amount may be achieved by administering to a subject a medication as described herein, optionally in an irrigation fluid I, a supply 114B of medication N, and/or an inflation fluid E using a system and/or method of the present invention.

The present invention finds use in both veterinary and medical applications. The term "subject" is used interchangeably herein with the term "patient". Suitable subjects of the present invention include, but are not limited to mammals of all ages. The term "mammal" as used herein includes, but is not limited to, primates (e.g., simians and humans), non-human primates (e.g., monkeys, baboons, chimpanzees, gorillas), bovines, ovines, caprines, ungulates, porcines, equines, felines, canines, lagomorphs, pinnipeds, rodents (e.g., rats, hamsters, and mice), etc. In some embodiments, the subject is a mammal and in certain embodiments the subject is a human. Human subjects include both males and females and subjects of all ages including fetal, neonatal, infant, juvenile, adolescent, adult, and geriatric subjects.

A system and/or method of the present invention may also used and/or carried out on animal subjects, particularly mammalian subjects such as mice, rats, dogs, cats, livestock and horses for veterinary purposes and/or for drug screening and/or drug development purposes.

As used herein, "monolithic" means an object that is a single, unitary piece formed or composed of a material without joints or seams. Alternatively, a unitary object can be a composition composed of multiple parts or components secured together at joints or seams.

With reference to FIGS. 1-13F, a sinus treatment system 10 according to embodiments of the invention is shown therein. The system 10 includes sinus treatment instrument system 100 and, optionally, an endoscope 20. The system 10 and the instrument system 100 can be used to conduct procedures (e.g., surgical procedures) on and/or treatment of sinuses. In particular, the system 10 and the instrument system 100 can be used to conduct surgical procedures on and treatment of the paranasal sinuses of a human patient (subject). The system 10 and the instrument system 100 can be used to conduct balloon sinoplasty or balloon dilation of sinus ostia and drainage pathways of a patient. In some embodiments, the system 10 and the instrument system 100 can be used to administer one or more medications to a patient, optionally into a sinus of the patient.

As described herein, the instrument system 100 can be used to execute multiple different operations, namely: an aspiration operation; a fluid delivery operation (irrigation fluid and/or medication); a dilation operation; and an illumination operation. Each of these operations can be executed using the instrument system 100 simultaneously (i.e., at the same time) or independently, in any desired combination. By "independently", it is meant that the operation can be selectively conducted while selectively not conducting another of the operations.

The instrument subsystem 100 includes a handheld instrument 120, a suction (negative pressure or vacuum) source 110, an irrigation fluid source 112, a medication source 114, and an inflation fluid source 116.

The suction source 110 may include a pump or compressor such as an electric pump or compressor, a syringe, or any other suitable device for generating a negative pressure (vacuum) to enable aspiration. In some embodiments, the suction source 110 generates and maintains a substantially constant negative pressure. The pressure level may be set by the operator.

Figure 12A:
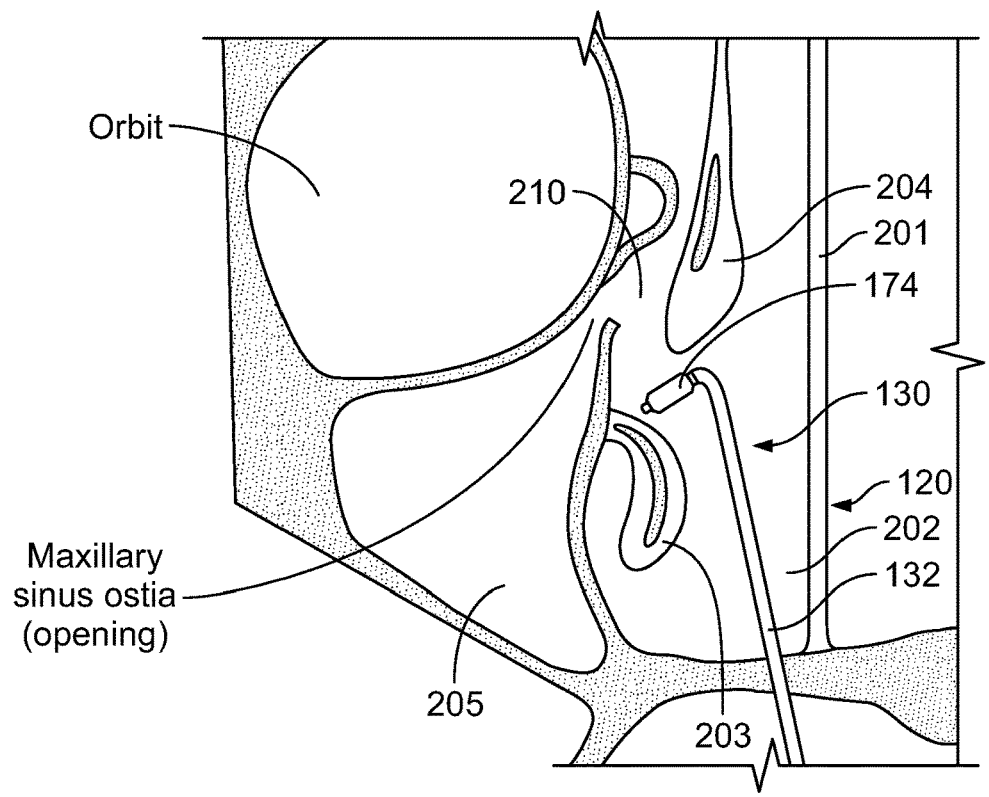
FIGS. 12A-13F illustrate methods using the sinus treatment system of FIG. 1.
Figure 12B:
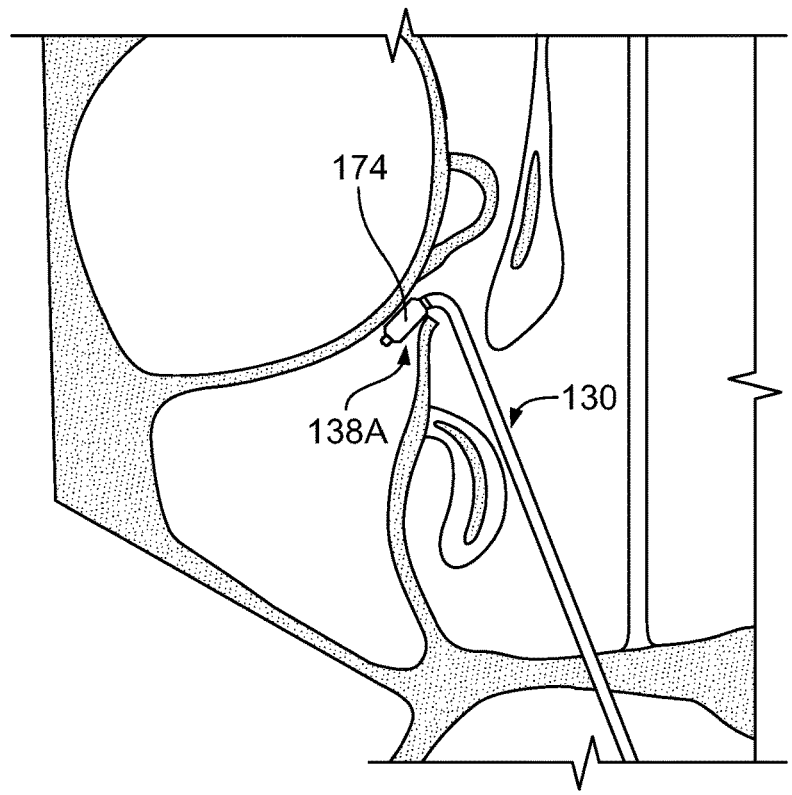
Figure 12C:
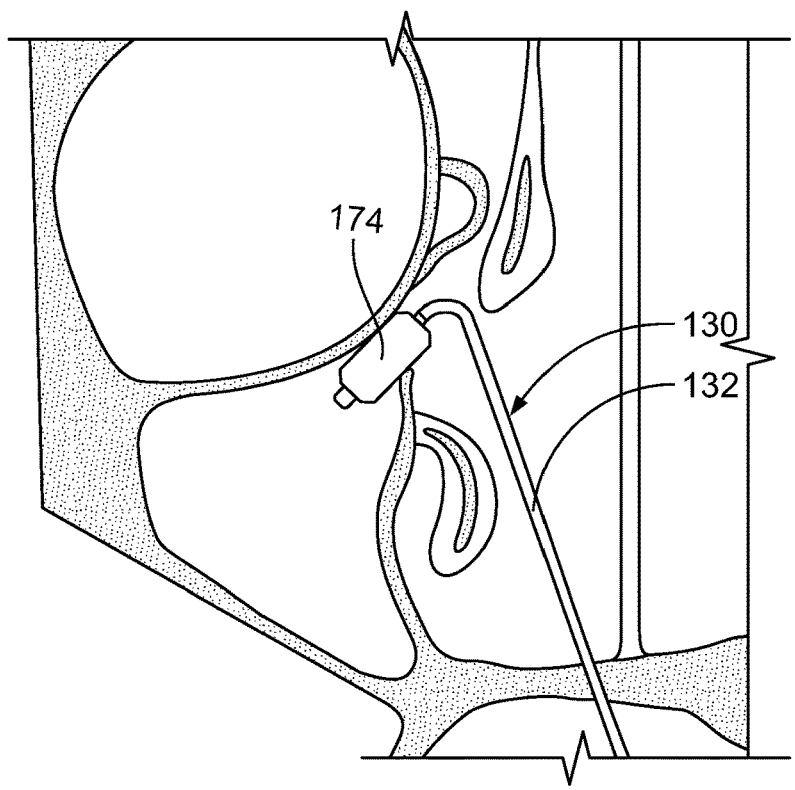
Figure 12D:
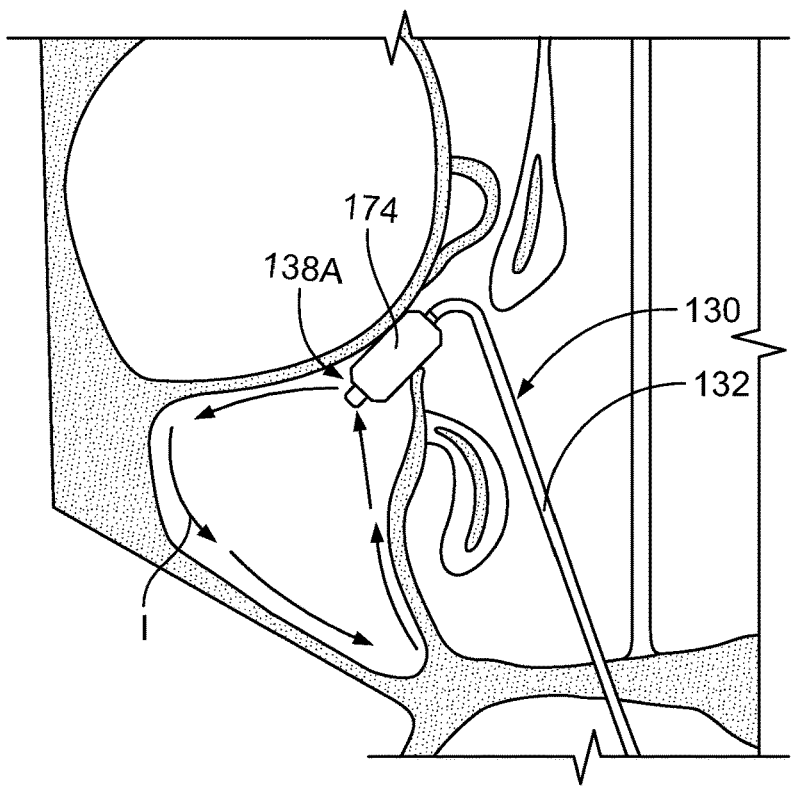

The irrigation fluid source 112 may include a pump 112A and a supply 112B of irrigation fluid I (FIG. 12D). The irrigation fluid I may be any suitable fluid and, in some embodiments, is an irrigation liquid. In some embodiments, the irrigation fluid I is water or saline. In some embodiments, the irrigation fluid source 112 is a syringe containing the irrigation fluid supply 112B. The irrigation syringe may be a hand-operated syringe. In some embodiments, the irrigation fluid I comprises a medication.

Figure 12E:
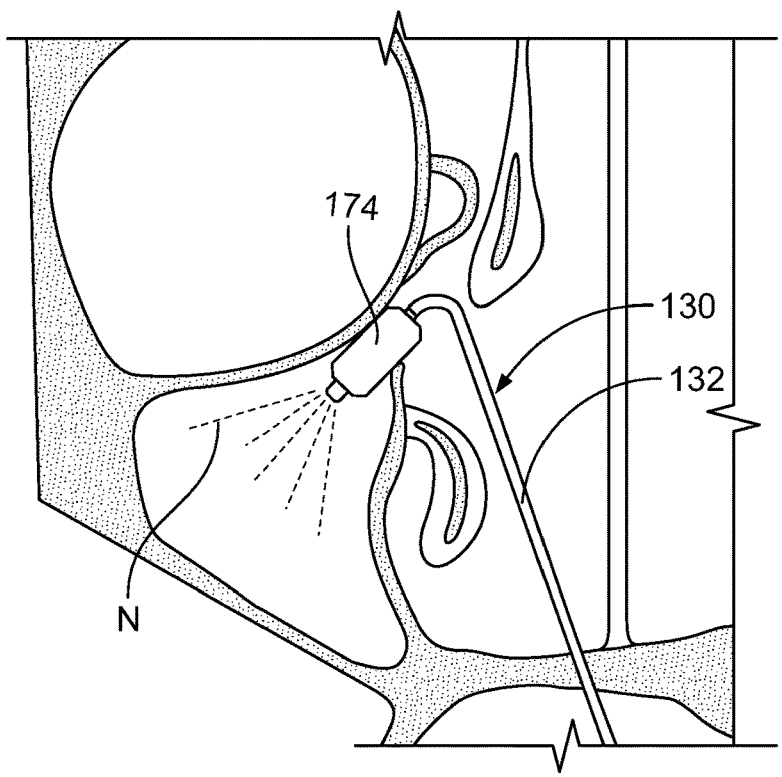

The medication source 114 may include a pump 114A and a supply 114B of medication N (FIG. 12E). The medication N may be any suitable flowable medication and, in some embodiments, is a liquid. In some embodiments, the medication is a medication fluid. In some embodiments, the medication source 114 is a syringe containing the medication supply 114B. The medication syringe may be a hand-operated syringe.

The inflation fluid source 116 may include a pump 116A and a supply 116B of inflation fluid E (FIG. 1). The inflation fluid may be any suitable fluid and, in some embodiments, is an inflation liquid. In some embodiments, the inflation fluid E is water or saline. In some embodiments, the inflation fluid source 116 is a syringe containing the inflation fluid supply 116B. The inflation syringe may be a hand-operated syringe. In some embodiments, an inflation fluid E comprises a medication.

"Medication" as used herein refers to a therapeutic and/or diagnostic agent. One or more medication(s) (e.g., one or more therapeutic(s) and/or one or more diagnostic agent(s)) may be present in the irrigation fluid I, the supply 114B, and/or the inflation fluid E. A medication may be in any suitable form. In some embodiments, a medication is present in a solution (e.g., an aqueous solution), suspension, or emulsion. In some embodiments, the medication source 114 is not present when a medication is not needed or is not to be administered and/or when a medication is present in the irrigation fluid I and/or inflation fluid E. "Therapeutic" as used herein refers to any chemical and/or biological compound and/or agent that can be used to treat and/or prevent a disease, disorder, or condition and/or a symptom thereof in a subject. Therapeutics include, but are not limited to, antibiotics, antiviral agents, antiparasitic agents, antifungal agents, anti-inflammatory agents, decongestants, mucous thinning agents, and/or steroids. "Diagnostic agent" as used herein refers to any substance that aids in the diagnosis of a disease, disorder or condition in a subject and/or that aids in the delivery of a therapeutic and/or device or component thereof to a subject. Diagnostic agents include, but are not limited to, contrast agents and/or imaging agents. In some embodiments, a medication may be one or more diagnostic or therapeutic substances such as those as described in U.S. Pat. No. 7,361,168 and optionally a method of administering and/or delivering a medication to a subject may be as described in U.S. Pat. No. 7,361,168, which is incorporated herein by reference for the teachings relevant to this paragraph.

A medication may be administered and/or delivered to a subject using any means and/or method known to those of skill in the art. In some embodiments, a medication may be administered and/or delivered to a subject via a fluid (e.g., a solution (e.g., an aqueous solution), suspension, emulsion, etc.) comprising the medication. The fluid may be an irrigation fluid I, a fluid provided in supply 114B, and/or an inflation fluid E. In some embodiments, the inflation fluid E comprises a medication and the inflation fluid E is administered to a subject through a balloon 174, 374 (discussed below). The balloon 174, 374 may comprise one or more pore(s) and the inflation fluid E comprising at least one medication may flow out of the one or more pore(s) of the balloon 174, 374 and optionally into a sinus. In some embodiments, the one or more pore(s) may open and/or expand when the inflation fluid E is filling and/or has filled the balloon 174, 374, optionally to a given volume and/or pressure, and upon opening and/or expanding the inflation fluid E flows, leaks, weeps and/or the like from the one or more pore(s). In some embodiments, a medication is provided on the balloon 174, 374 such as, for example, in the form of a coating on the balloon 174, 374. The coating and/or medication may be administered to a subject upon contact with the coating such as, e.g., upon the balloon 174, 374 expanding and/or contacting a tissue and/or a nasal and/or sinus surface of the subject. In some embodiments, the coating and/or medication are administered to a subject upon the balloon 174, 374 blocking and/or plugging a sinus passage of the subject. In some embodiments, the system 10 and instrument 120 may administer and/or deliver an implant comprising a medication. The implant may be in the form of a coil, stent, spike, wire, mesh, patch, and/or the like. The system 10 and instrument 120 may attach the implant to a tissue and/or a nasal and/or sinus surface of a subject. In some embodiments, the system 10 and instrument 120 may embed the implant into a tissue and/or a nasal and/or sinus surface of a subject. In some embodiments, the implant is attached and/or embedded upon the balloon 174, 374 expanding and/or contacting a tissue and/or a nasal and/or sinus surface of the subject, optionally upon the balloon 174, 374 blocking and/or plugging a sinus passage of the subject. The implant may be biodegradable and/or bioabsorbable. The implant may comprise a medication and optionally a carrier material (e.g., a polymer). In some embodiments, an implant may be one as described in U.S. Pat. No. 7,361,168, and optionally may be delivered as described in U.S. Pat. No. 7,361,168, which is incorporated herein by reference for the teachings relevant to this paragraph.

The instrument 120 is a balloon dilation catheter device that includes functional features and mechanisms in addition to the dilation functionality. The instrument 120 includes a handheld unit or base 122, a probe (or guide member or extension assembly) 130, a lighting system 150, an aspiration system 160, a delivery system 165, a dilation system 170, and a connector fitting 178. The instrument 120 has a proximal end 120A and a distal end 120B defining a primary or longitudinal axis L-L.

Base 122 has a main axis M-M substantially parallel to the instrument longitudinal axis L-L.

The base 122 includes a housing 124 including opposed parts 124B defining an internal cavity 124A. Suitable features such as channels, cavities, posts and the like may be provided in the base 122 and the cavity 124A to receive, position and secure the various components housed in the base 122, as described herein.

The housing 122 has a main section 126 extending from a proximal end 126A to a distal end 126B parallel to the main axis M-M. A distal port 127 is defined in the distal end 126B.

The base 122 further includes a handle section 128 that defines a handle axis H-H transverse to the main axis M-M. The handle section 128 has an inner end 128B that merges with the main section 126 and an opposing outer end 128A. In some embodiments, the handle axis H-H forms an angle A1 (FIG. 3) with the main axis M-M in the range of from about 50 to 130 degrees and, in some embodiments, in the range of from about 70 to 110 degrees. In some embodiments, the handle axis H-H is substantially perpendicular to the main axis M-M and the instrument longitudinal axis L-L.

The base 122 is ergonomically shaped or contoured to have a rear handle face 129A, a top face 129B, an upper shoulder 129C, a lower front handle face 129D, an upper front handle face 129E, and a middle front handle face 129F. The face 129A is located rearward of the top face 129B and connected thereto by the rounded transition or shoulder face 129C. The middle front handle face 129F projects forwardly beyond the lower front handle face 129D and the upper front handle face 129E.

The probe 130 includes an elongate shaft 132 defining a longitudinal probe axis P-P extending from a proximal end 132A to a distal end 132B. The probe axis P-P is substantially parallel to the instrument axis L-L and the main axis M-M. The shaft 132 includes a dilator section 136, an intermediate section 137, and a tip section 138. The tip section 138 terminates at a tip 138A.

The shaft 132 has an outer surface 134A. In some embodiments, the outer surface 134A is substantially cylindrical. In some embodiments, the outer surface 134A is substantially conical or frusto-conical. In some embodiments, the outer surface 134A is substantially elliptical in lateral cross-section and, in some embodiments, is substantially circular in lateral cross-section.

The shaft 132 may be formed of any suitable material(s). In some embodiments, the shaft 132 is formed of a stainless steel hypotube.

In some embodiments, the shaft 132 is unitary. In some embodiments, the shaft 132 is unitarily formed. In some embodiments, the shaft 132 is monolithic. The shaft 132 may be molded (e.g., injection molded) or extruded.

In some embodiments, the shaft 132 is formed of a rigid but malleable material. This permits the shaft 132 to be deliberately bent into a new shape or configuration in response to application of a sufficient bending force, and to retain the original or new shape or configuration when a lesser force is applied to the shaft 132. In some embodiments, the required bending force is greater than any force the shaft 132 is expected or intended to experience in service during the surgical procedure (i.e., during navigation or use of the probe 120 within the anatomy of the patient). The malleability of the shaft 132 may enable the user to bend the shaft 132 into a desired angle or curvature to achieve proper positioning for the balloon 174 and the distal end tip 138A in the sinus ostia or sinus drainage pathways.

In some embodiments, the shaft 132 is pre-shaped to have a curved distal portion (e.g., as shown in FIGS. 12A-12E). The curved distal portion may be configured to match with the frontal sinus outflow tract or frontal recess.

In some embodiments, the distal portion the shaft 132 is formed right to the distal end 132B and may have a radius of curvature in the range of from about 0.25 inch to about 1.5 inch and, in some embodiments, from about 0.75 to about 1.25 inch.

The shaft 132 extends a predetermined or prescribed distance or length L1 (FIG. 3) from the base 122 to the distal end 132B. In some embodiments, the length L1 is in the range of from about 4 to 12 inches and, in some embodiments, from about 8 to 10 inches.

In some embodiments, the shaft 132 has an outer diameter D1 (FIG. 6) in the range of from about 1 to 5 mm and, in some embodiments, from about 1.5 to 3.3 mm.

In some embodiments, the shaft 132 has a nominal wall thickness T1 (FIG. 6) in the range of from about 0.001 to 0.030 inch and, in some embodiments, from about 0.005 to 0.020 inch.

In some embodiments, the distal tip 138A has an outer diameter in the range of from about 0.5 to 5 mm and, in some embodiments, from about 1 to 3.3 mm.

In some embodiments, the edges of the tip 138A are rounded or smooth to prevent or reduce trauma to the mucosa of the sinuses.

A lighting lumen 140, an aspiration lumen 142, and a delivery lumen 144 are defined in the shaft 132. The each of the lumens 140, 142, 144 is contained or located within the boundary defined by the shaft outer surface 134A. The lumens 140, 142, 144 are elongate and extend radially or laterally side-by-side relative to one another along the axis P-P. In some embodiments, the lumens 140, 142, 144 extend substantially parallel to one another along the axis P-P.

The lighting lumen 140 terminates at a proximal opening 140A at the end 132A and at a distal opening 140B at the end 132B. The aspiration lumen 142 terminates at a proximal opening 142A at the end 132A and at a distal opening or aspiration inlet port 142B at the end 132B. The delivery lumen 144 terminates at a proximal opening 144A at the end 132A and at a distal opening or fluid delivery outlet port 144B at the end 132B. The distal openings 140B, 142B, 144B are formed in the tip 138A.

In some embodiments, each lumen 140, 142, 144 is substantially uniform in size and cross-sectional area throughout its length and including its proximal and distal end openings. In other embodiments, one or more of the lumens 140, 142, 144 may be nonuniform.

Figure 10:
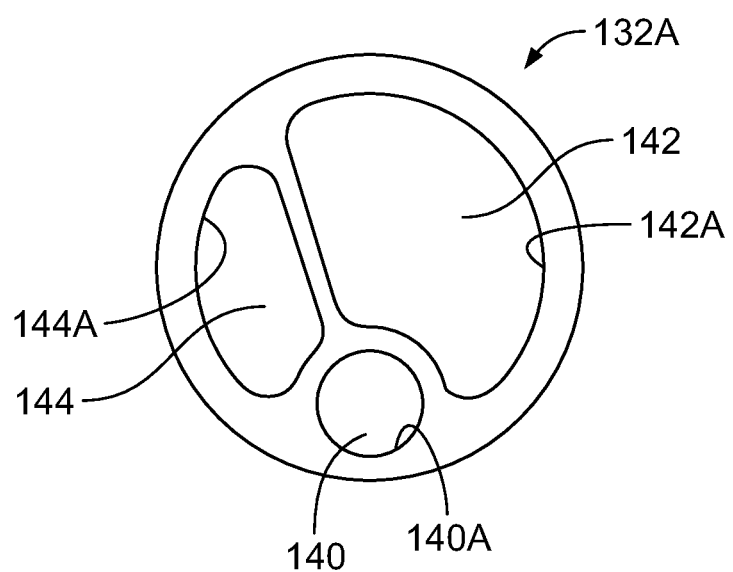
FIG. 10 is a proximal end view of a shaft forming a part of the instrument of FIG. 2.
Figure 11:
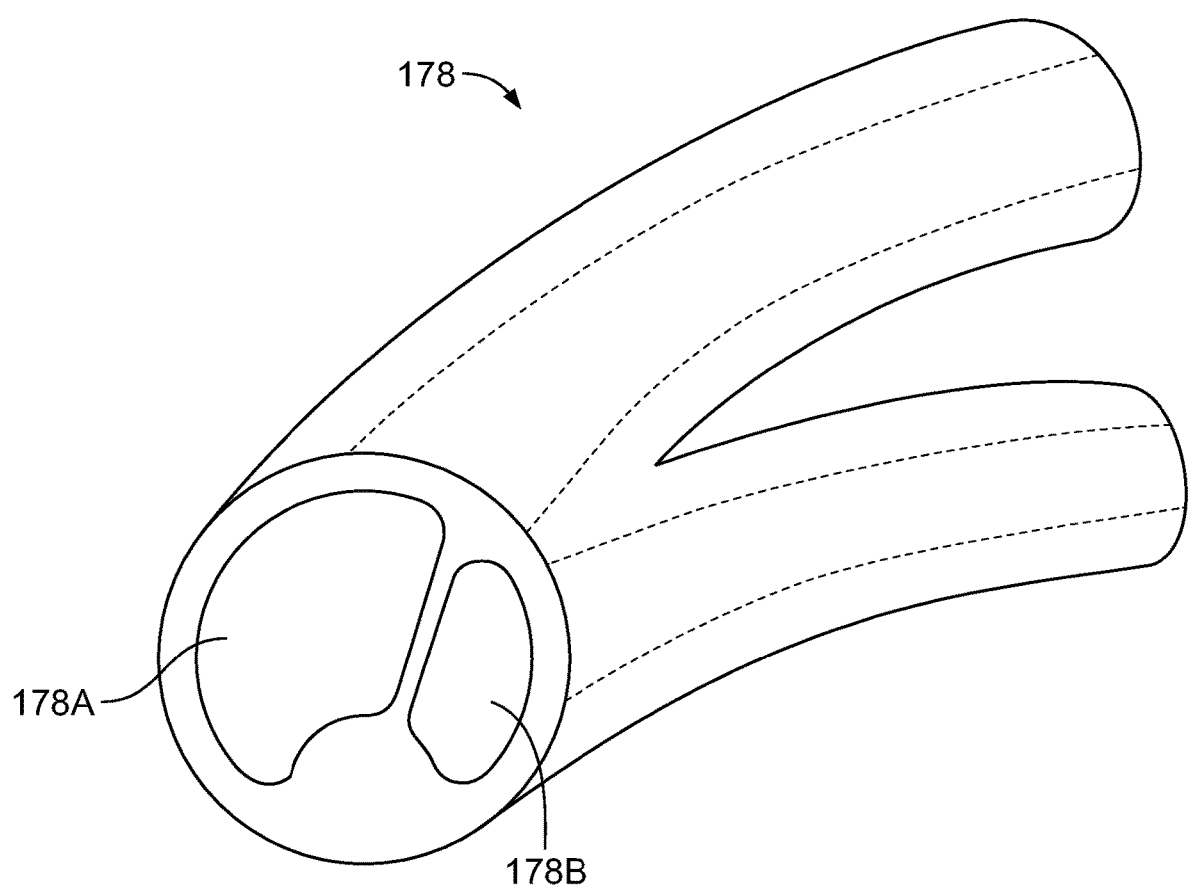
FIG. 11 is a rear perspective view of a fitting forming a part of the instrument of FIG. 2.

In some embodiments and as shown in FIG. 10, one or more of the lumens 140, 142, 144 may have a different cross-section shape and/or area than another of the lumens 140, 142, 144. In some embodiments and as shown in FIG. 10, one or more of the lumens 140, 142, 144 may have an irregular or asymmetric shape (e.g., non-elliptical and non-annular) that more closely optimizes the use of the available area within the shaft 132.

With reference to FIG. 10, in some embodiments the cross-sectional area of the aspiration lumen 142 is greater than the cross-sectional area of the delivery lumen 144. In some embodiments, the cross-sectional area of the aspiration lumen 142 is at least 1.5 times the cross-sectional area of the delivery lumen 144. In some embodiments, the cross-sectional area of the aspiration lumen 142 is in the range of from about 2 to 4 times the cross-sectional area of the delivery lumen 144.

In some embodiments, the cross-sectional area of the aspiration lumen 142 is greater than the cross-sectional area of the lighting lumen 140. In some embodiments, the cross-sectional area of the aspiration lumen 142 is at least 15 times the cross-sectional area of the lighting lumen 140. In some embodiments, the cross-sectional area of the aspiration lumen 142 is in the range of from about 8 to 40 times the cross-sectional area of the lighting lumen 140.

In some embodiments, the cross-sectional area of the delivery lumen 144 is greater than the cross-sectional area of the lighting lumen 140. In some embodiments, the cross-sectional area of the delivery lumen 144 is at least 8 times the cross-sectional area of the lighting lumen 140. In some embodiments, the cross-sectional area of the delivery lumen 144 is in the range of from about 4 to 10 times the cross-sectional area of the lighting lumen 140.

In some embodiments, the cross-sectional area of the aspiration lumen 142 is in the range of from about 0.28 to 1.76 $mm^2$.

In some embodiments, the cross-sectional area of the delivery lumen 144 is in the range of from about 0.07 to 0.8 $mm^2$.

In some embodiments, the cross-sectional area of the lighting lumen 140 is in the range of from about 0.007 to 0.2 $mm^2$. In some embodiments, the cross-sectional area of the lighting lumen 140 is substantially the same as the outer diameter of the waveguide 154 (including the sheath).

In some embodiments, the cross-sectional area of the through passage or lumen of the inflation conduit 172 is less than the cross-sectional area of the aspiration lumen 142 and, in some embodiments, less than the cross-sectional areas of the delivery lumen 144 and the lighting lumen 140.

The connector fitting 178 (FIGS. 2, 5 and 11) includes an aspiration channel 178A and a delivery channel 178B each extending fully therethrough. The distal end of the fitting 178 is mated and secured to the proximal end 132A of the shaft 132 such that the distal opening of the aspiration channel 178A is fluidly connected to the aspiration lumen 142, and the distal opening of the delivery channel 178B is fluidly connected to the delivery lumen 144. The fitting 178 may be formed of any suitable material (e.g., metal) and may be secured to the proximal end of the shaft 132 by any suitable technique (e.g., welding or adhesive).

The integral lighting system 150 includes a light source 151, an internal battery 152, and a waveguide 154. In some embodiments, the light source 151, the battery 152 and a battery contact spring are mounted in the cavity 124A of the base 122. In some embodiments, the light source 151 includes a light emitting diode (LED) and may include an associated printed circuit board (PCB).

In some embodiments, the waveguide 154 is an optical fiber (e.g., a polymeric or glass optical fiber). The waveguide 154 may be an optical fiber including a core and a surrounding cladding and may be configured to provide total internal reflection. The waveguide 154 may be surrounded by a sheath to protect the waveguide and prevent light loss. A light emitting guide wire such as that disclosed in U.S. Patent Application Publication No. 2007/0249896, which is incorporated by reference herein, can be used as the waveguide 154.

The waveguide 154 extends from a proximal end 154A in the base 122 and proximate the light source 151, through the opening 140A, through the lighting lumen 140, and to a distal end 154B adjacent the distal end 132B. The waveguide 154 has an end face 154C at the distal end 154B, from which light is emitted. The end face 154C may be polished. In some embodiments, the waveguide distal end 154B is located substantially flush with the distal end 132B. In other embodiments, the waveguide distal end 154B extends outwardly beyond the distal end 132B a distance in the range of from about 1 to 5 cm.

Figure 4:
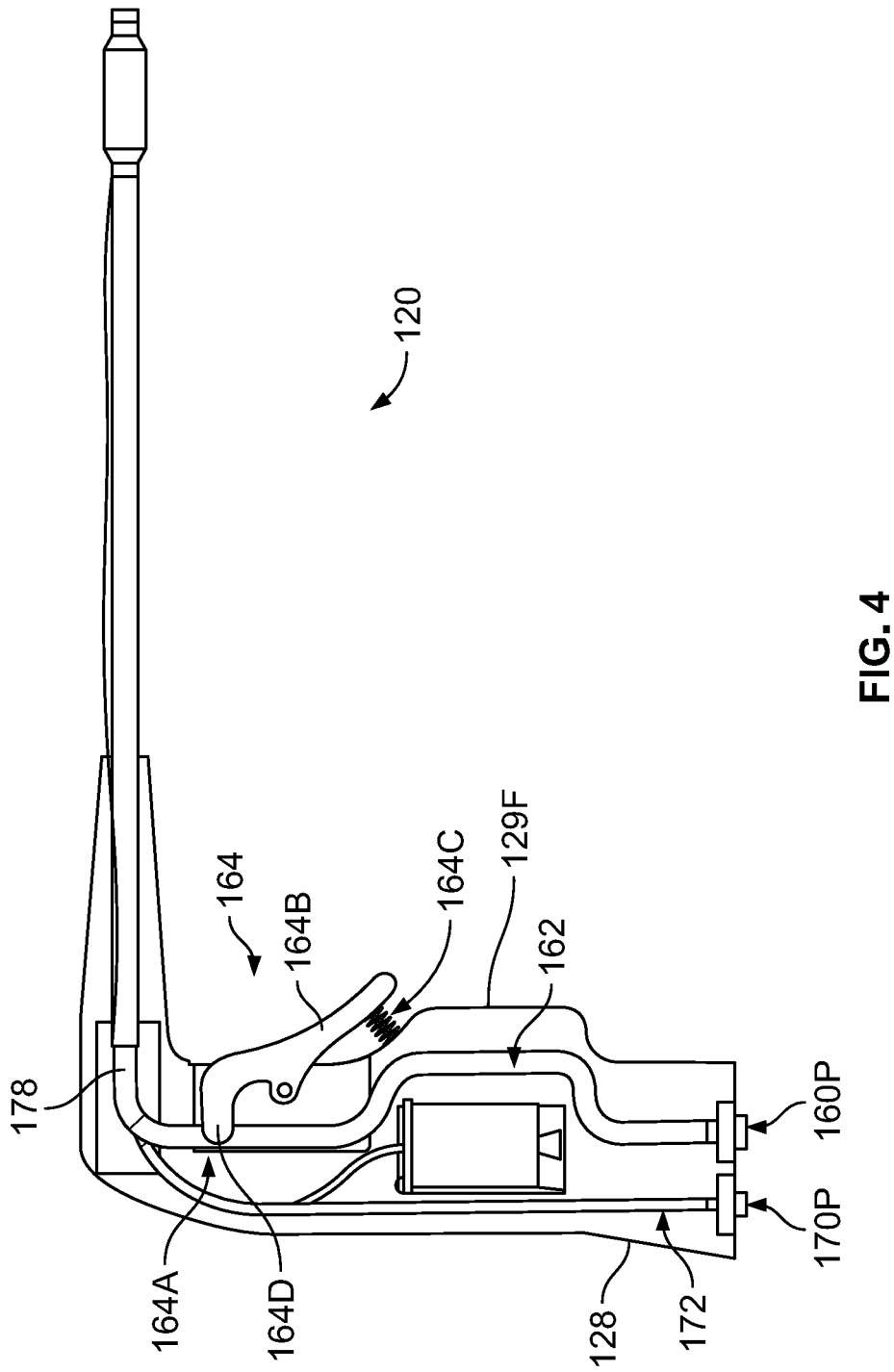
FIG. 4 is a fragmentary, side view of the instrument of FIG. 2.
Figure 5:
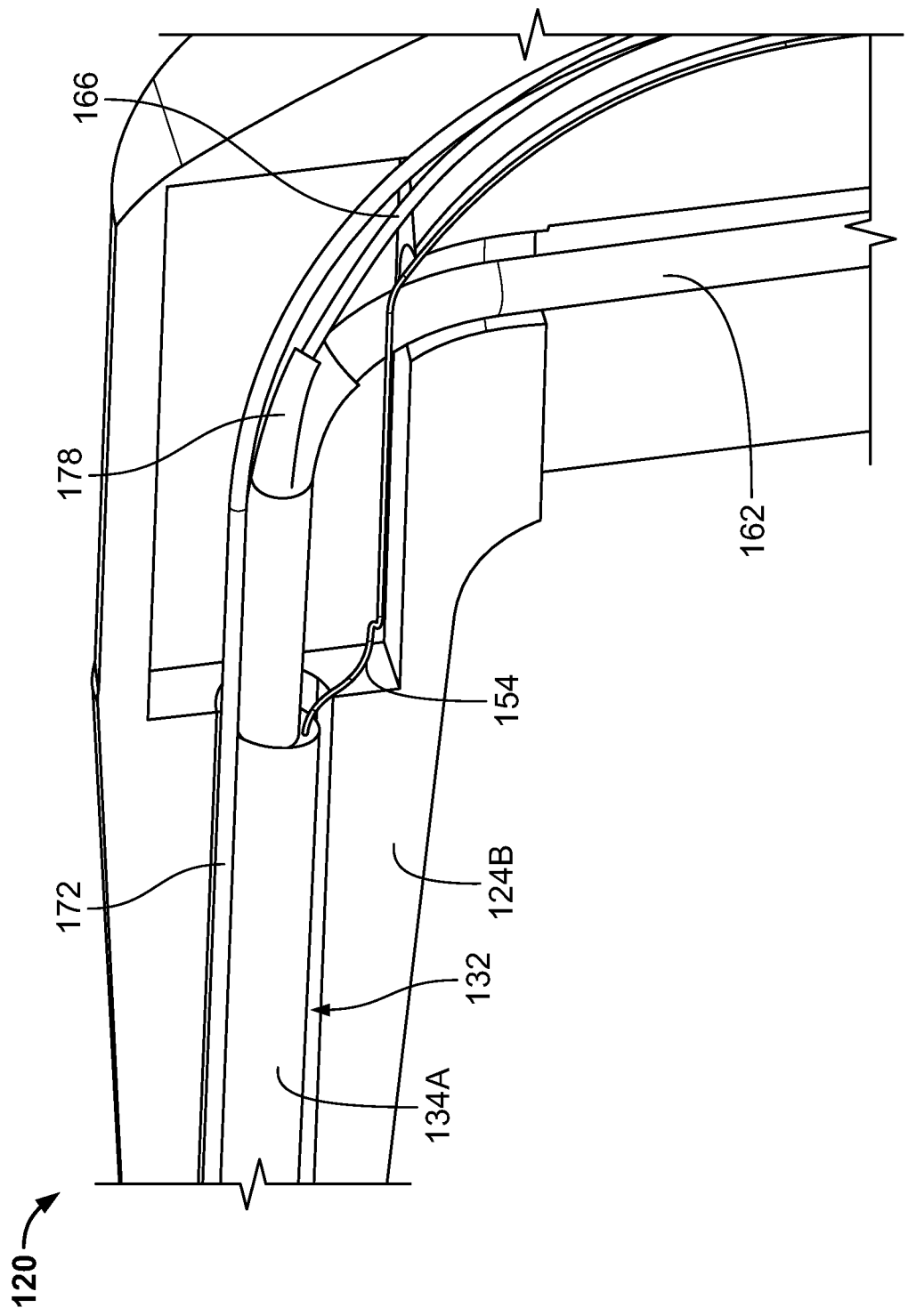
FIG. 5 is a fragmentary, rear perspective view of the instrument of FIG. 2.

As shown in FIGS. 1 and 4, an electrically insulating switch tab 151A electrically disconnects a terminal of the battery 152 from the lighting circuit until it is desired to operate the light source 151. In use, the operator removes the tab 151A, thereby actuating the light source 151 to generate light that is transmitted through the waveguide 154 and emitted from the distal end 154B. Alternatively, the lighting system 150 may include a light switch to turn the light source on and off.

In some embodiments, the instrument 120 may include an external power supply (e.g., connected to the instrument 120 by a power cord) in place of or in addition to the battery 152.

The aspiration system 160 includes a conduit 162, a suction port 160P, and an aspiration controller 164. The suction port 160P is provided in the outer end of the handle 128. The conduit 162 extends through the handle 128. A proximal end of the conduit 162 is fluidly connected to the suction port 160P. The distal end of the conduit 162 is fluidly coupled to the aspiration channel 178A of the connector fitting 178, and is thereby fluidly connected to the proximal opening 142A of the aspiration lumen 142. The suction source 110 is fluidly connected to the suction port 160P by a conduit 160T. The suction port 160P may be provided with a connector or coupling (such as a Luer lock) to fluidly connect the conduit 160T from the suction source 110 to the port 160P.

The aspiration controller 164 includes a valve 164A in the base 122, an integral trigger 164B attached to the base 122, and a return spring 164C. The trigger 164B is operable to selective allow and prevent fluid flow between the lumen 142 and the suction source 110 through the conduit 162.

In some embodiments and as shown, the valve 164A is a pinch valve. The trigger 164B is positioned proximate the handle 128 such that the trigger 164B can be conveniently pulled using the operator's finger. A portion 164D of the trigger 164B serves as a pinching feature that compresses and closes the conduit 162 when the trigger 164B is not depressed. When the trigger 164B is depressed, the conduit 162 is opened. Upon release, the trigger 164B is urged back to the closed position by the spring 164C. The trigger 164B thereby operates as a hand-actuated valve 164A that can be selectively operated by the user to open and close the fluid pathway between the suction source 110 and the lumen 142.

In alternative embodiments, the trigger 164B is configured such that its operation is reversed. In that case, the conduit 162 is open by default. When the trigger 164B is depressed, the conduit 162 is closed. Upon release, the trigger 164B is urged back to the open position by the spring 164C.

The delivery system 165 includes a conduit 166, a delivery port 165P, and a delivery controller 168 (for irrigation fluid) or a delivery controller 169 (for medication). The delivery port 165P is provided in the outer end of the handle 128. The conduit 166 extends through the handle 128. A proximal end of the conduit 166 is fluidly connected to the delivery port 165P. The distal end of the conduit 166 is fluidly coupled to the delivery channel 178B of the connector fitting 178, and is thereby fluidly connected to the proximal opening 144A of the delivery lumen 144. The delivery source 112 is fluidly connected to the delivery port 165P by a conduit 165T. The delivery port 165P may be provided with a connector or coupling (such as a Luer lock) to fluidly connect a conduit 165T from the irrigation fluid source 112 to the port 165P.

The delivery controller 168 is operable to control actuation of the delivery source 112 and/or to selectively allow and prevent fluid flow through the conduits 166, 165T to the delivery lumen 144. In some embodiments, the controller 168 is offboard from the instrument 120. In some embodiments, the delivery source 112 is embodied in a syringe that includes a reservoir (supply 112B) and a pump mechanism (pump 112A and controller 168). In some embodiments, the syringe is a hand operated syringe. The medication delivery controller 169 can be likewise constructed and operated to control delivery of medication from the source 114.

The dilation system 170 includes a dilator mechanism 171 (in the form of a balloon 174), a conduit 172, an inflation port 170P, and a dilation controller 176. The balloon 174 is mounted proximate the distal end 132B of the shaft 132. The dilation system 170 is configured to selectively inflate and deflate the balloon 174 on demand by the operator.

The inflation port 170P is provided in the outer end of the handle 128. The conduit 172 extends through the handle 128. A proximal end of the conduit 172 is fluidly connected to the inflation port 170P. The inflation source 116 is fluidly connected to the inflation port 170P by a conduit 170T. The inflation port 170P may be provided with a connector or coupling (such as a Luer lock) to fluidly connect a conduit 170T from the inflation source 116 to the port 170P.

A connecting section of the conduit 172 extends along the outer surface 134A of the shaft 132 from the handle 128 to the balloon 174. The distal end of the conduit 172 extends into the balloon 174 through a port 175 defined between the balloon 174 and the outer diameter of the shaft 132. The connecting section may be secured to the shaft 132 by tape, adhesive, welding, or any other suitable method.

The balloon 174 includes sealed ends 174B, a main section 174A therebetween, and an outer surface 174C. In some embodiments, the balloon 174 is mounted directly on the shaft 132 so as to form a fluidic seal between the two components. The balloon 174 may be bonded to the shaft 132 using a weld, adhesive, or the like. Alternatively, the balloon 174 may be secured to the shaft 132 using a mechanical connection. The balloon 174 and the shaft 132 define a sealed balloon inflation chamber 177 therebetween.

The balloon 174 is pliable and expandable when inflated. The dilation system 170 can be operated to place the balloon 174 alternatively in at least a first, relatively radially non-expanded configuration (herein, the non-expanded position) and a second, radially expanded configuration (herein, the expanded configuration). In the expanded configuration, the outer diameter D2 (FIG. 8) of the balloon 174 is larger than in the deflated configuration.

In some embodiments and as will be appreciated from the description herein, the dilation system 170 can be operated to place the balloon 174 in a range of different expanded configurations. That is, the balloon 174 can be forced to assume one of a plurality of different expanded configurations each having a different outer diameter D2.

In some embodiments and as will be appreciated from the description herein, the non-expanded configuration of the balloon 174 may not be a fully non-expanded or deflated configuration. That is, the outer diameter of the balloon 174 may be greater than is smallest possible diameter in the non-expanded configuration.

Figure 6:
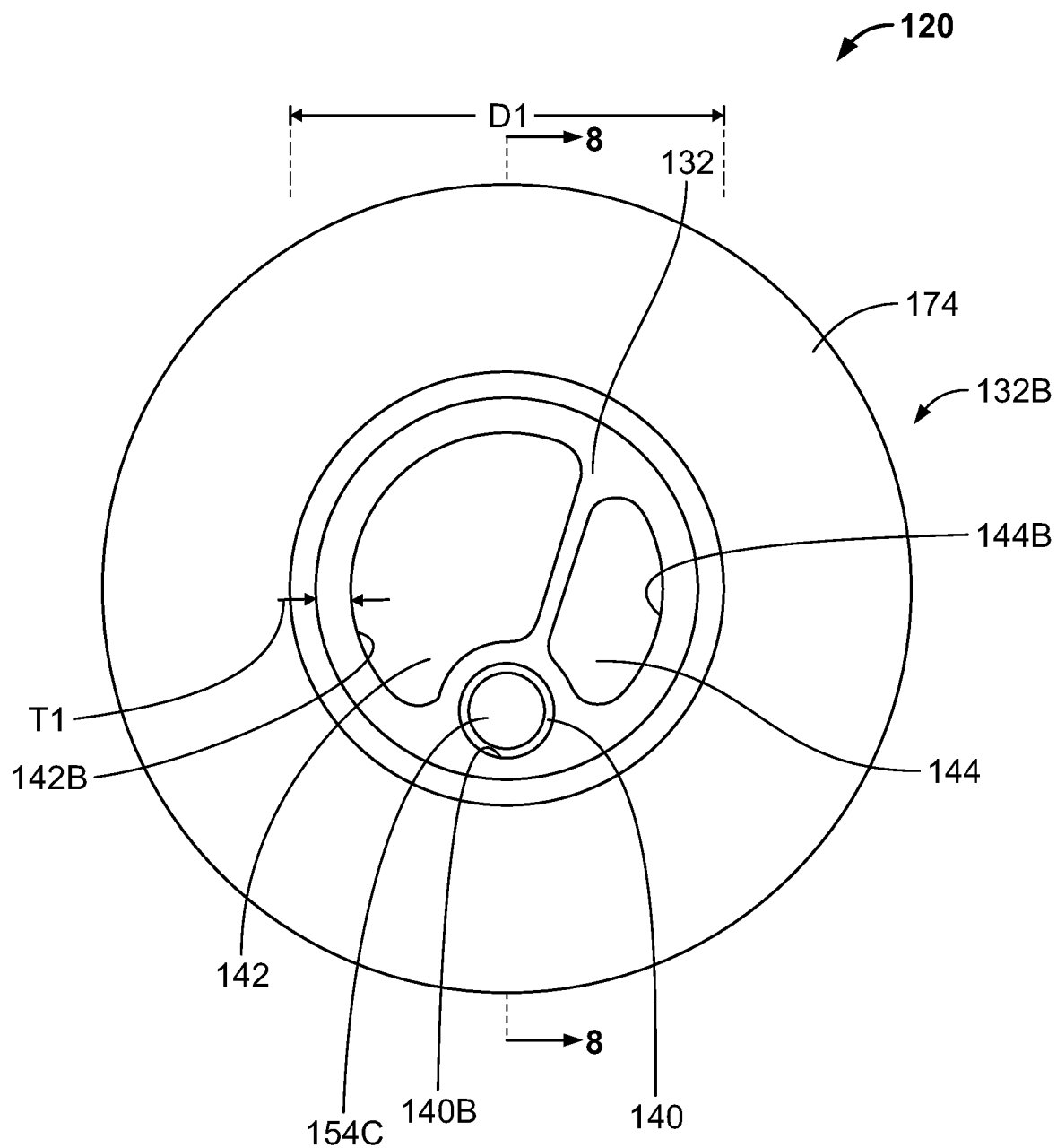
FIG. 6 is a distal end view of the instrument of FIG. 2, wherein a balloon of the instrument is in an expanded position.
Figure 7:
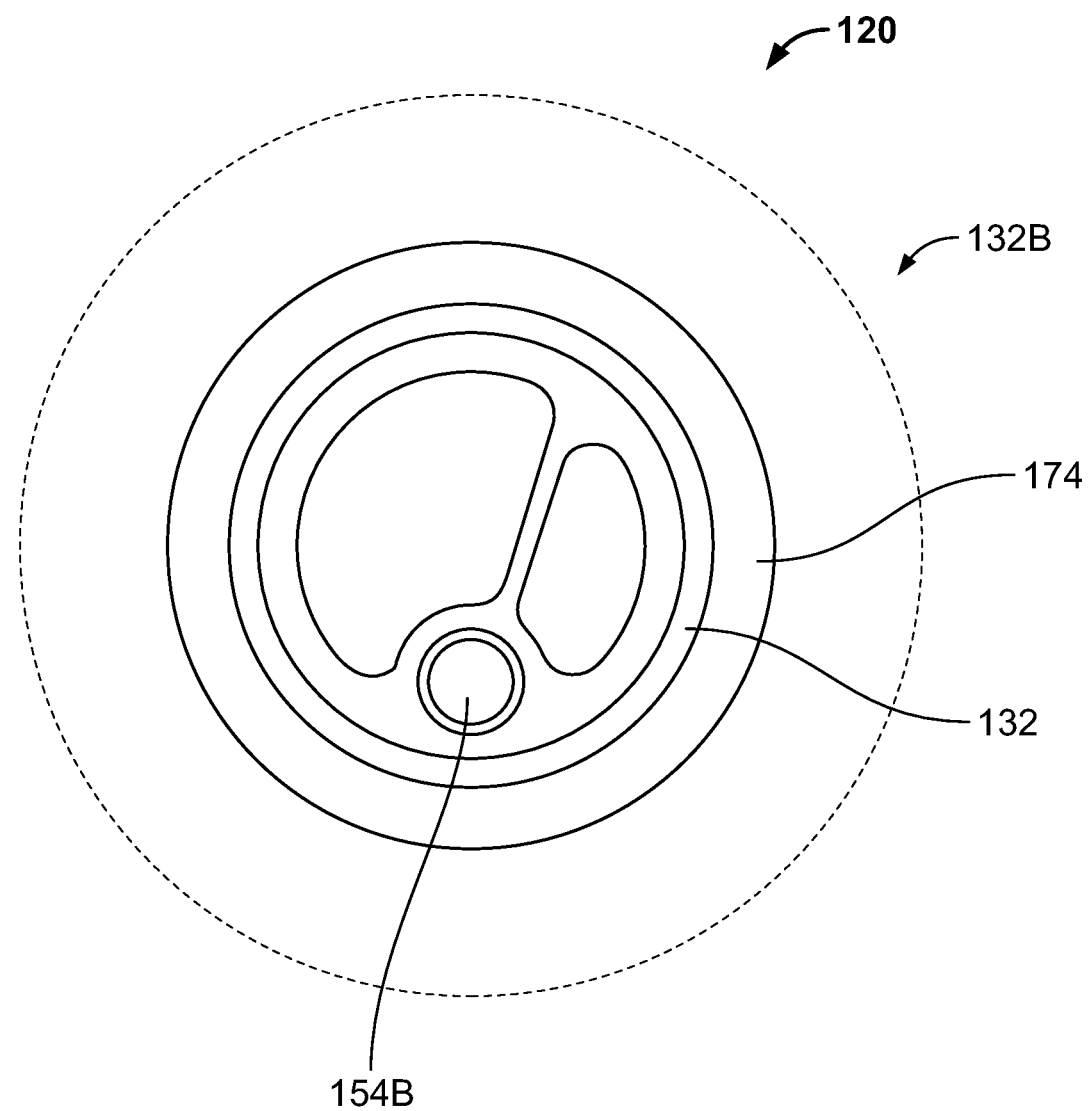
FIG. 7 is a distal end view of the instrument of FIG. 2, wherein the balloon is in a deflated position.
Figure 8:
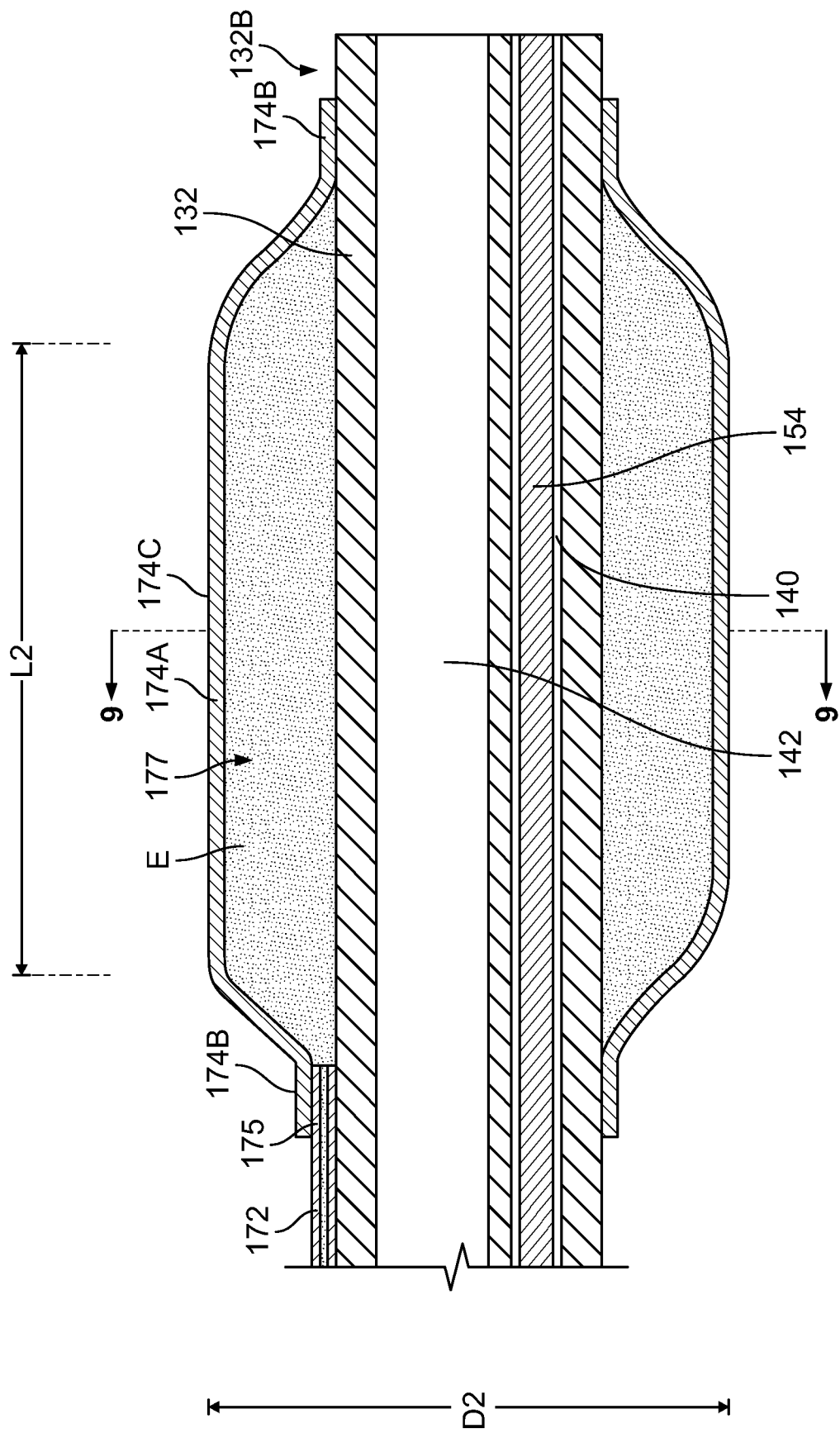
FIG. 8 is a cross-sectional view of the instrument of FIG. 2 taken along the line 8-8 of FIG. 6, wherein the balloon is in the expanded position.
Figure 9:
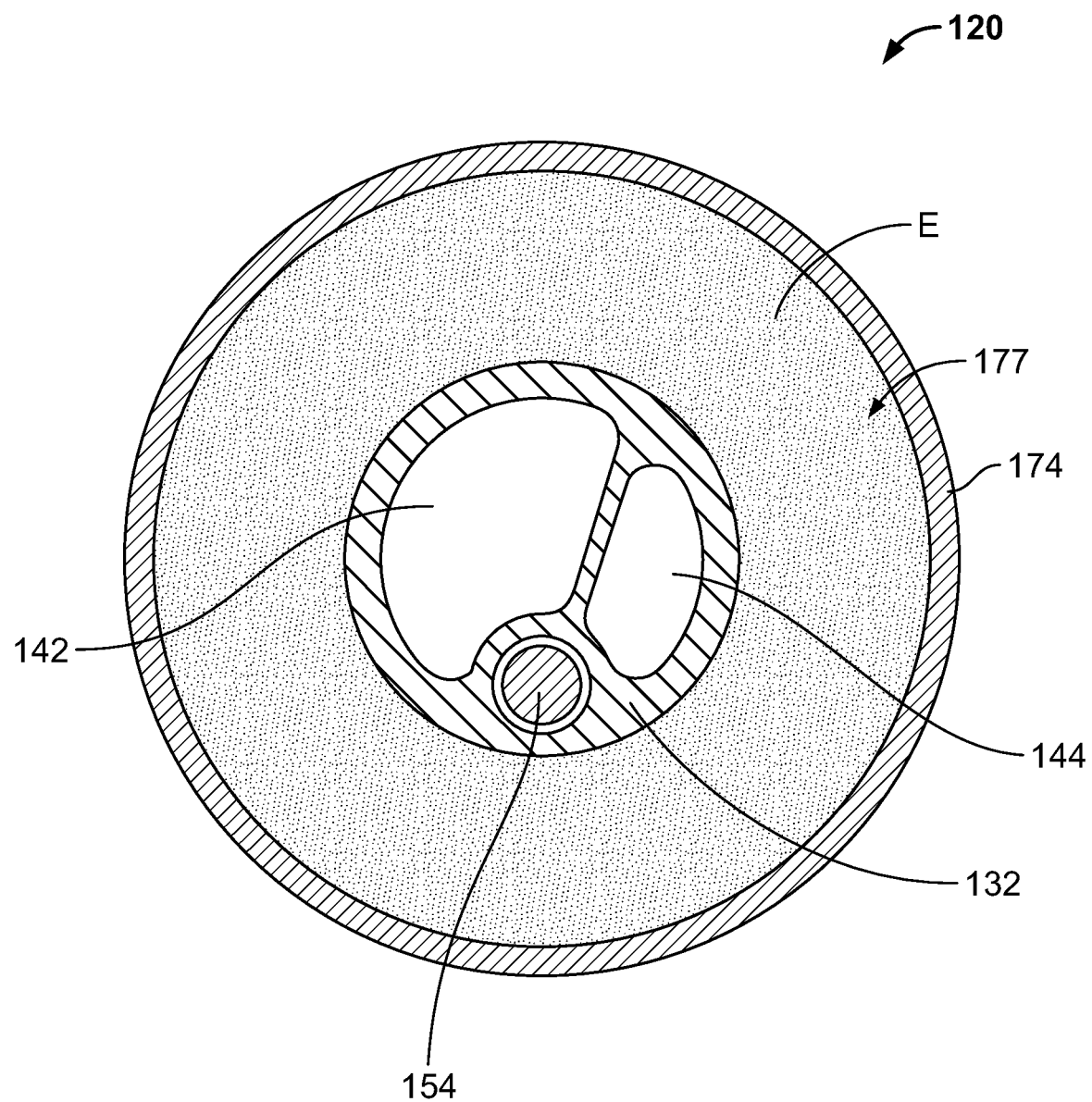
FIG. 9 is a cross-sectional view of the instrument of FIG. 2 taken along the line 9-9 of FIG. 8, wherein the balloon is in the expanded position.

In some embodiments, the main section 174A takes on a cylindrical shape when the balloon 174 is substantially fully inflated (e.g., as shown in FIGS. 6, 8 and 9). In some embodiments, the end sections 174B take on a frusto-conical shape when the balloon 174 is substantially fully inflated. However, other shapes may be utilized depending upon the target anatomy.

In some embodiments, the balloon 174 when fully inflated has an outer diameter D2 in the range of about 3 mm to about 9 mm.

In some embodiments, the balloon 174 when fully inflated has a fully inflated length L2 in the range of about 10 mm to 25 mm.

The balloon 174 may be formed of any suitable material. In some embodiments, the balloon 174 is formed of high strength but flexible polymeric material such as a polyamide (e.g., nylon), PEBAX or the like. The balloon 174 may be "blow molded" to a relatively thin wall thickness, and capable of holding relatively high pressures from about 6 atmospheres to about 28 atmospheres of inflation pressure.

The dilation controller 176 is operable to control actuation of the inflation fluid source 116 to selectively force inflation fluid E flow through the conduits 172, 170T to the balloon 174 to expand the balloon 174 and, alternatively, permit (or forcibly draw) fluid flow from the balloon 174, through the conduits 172, 170T to deflate the balloon 174.

In some embodiments, the dilation controller 176 is offboard from the instrument 120. In some embodiments, the inflation fluid source 116 is embodied in a syringe that includes a reservoir (supply 116B) and a pump mechanism (pump 116A and dilation controller 176). In some embodiments, the syringe is a hand operated syringe. In some embodiments, the dilation controller 176 includes a closed loop fluid pump system. One exemplary inflation device that may be used to selectively inflate the balloon 174 is described in U.S. Published Patent Application No. 2010/0211007, which is incorporated by reference as if set forth fully herein. Other inflation devices may also be used.

The sinus treatment system 10 and the instrument 120 may be used as follows in accordance with methods of the invention.

The system 10 can be set up by connecting the conduits 160T, 165T, 170T to the ports 160P, 165P, 170P, respectively. The ports 160P, 165P, 170P may include disconnectable connectors. If an endoscope is to be used, the endoscope 20 may be set up as needed. If an irrigation step is to be executed, the conduit 165T is connected to the irrigation fluid source 112. If a medication delivery step is to be executed, the conduit 165T is connected to the medication source 114.

Generally, the lighting system 150 is activated by removing the tab 151A (or operating a light actuation switch on the instrument 120, if any), thereby permitting the battery 152 to power the LED 151. The light emitted by the LED 151 propagates through the waveguide 154 and is emitted from the waveguide 154 through the end face 154C. The illumination function of the instrument system 100 is thereby selected and actuated and can be used to execute on an illumination operation wherein light is emitted from the waveguide end face 154C (e.g., trans-illumination).

The aspiration system 160 is actuated and deactuated using the trigger 164B as described above. When the trigger 164B is depressed, the suction source 110 will generate a negative pressure (vacuum) in the aspiration lumen 142 and at the opening 142B. The negative pressure will induce an aspiration flow into the aspiration lumen 142 through the inlet port 142B, and out of the instrument 120 through the conduits 162, 160T. The aspiration function of the instrument system 100 is thereby selected and actuated and can be used to execute an aspiration operation. When the trigger 164B is released, the negative pressure and aspiration flow are terminated.

The delivery system 165 is actuated and deactuated using the irrigation controller 168 or the medication delivery controller 169, whichever is connected to the port 165P. The fluid delivery function of the instrument system 100 is thereby selected and actuated and can be used to execute a fluid delivery option. The fluid delivery operation can be an irrigation fluid delivery operation and/or a medication delivery operation.

If the irrigation system 112 is connected, the irrigation controller 168 is actuated to force a flow of the irrigation fluid I through the conduits 166, 165T and the delivery lumen 144, and out of the probe 130 through the outlet port 144A.

If the medication delivery system 114 is connected, the medication delivery controller 169 is actuated to force a flow of the medication N through the conduits 166, 165T and the delivery lumen 144, and out of the probe 130 through the outlet port 144A.

The dilation system 170 is actuated and deactuated using the dilation controller 176. In an inflation operation or step, the dilation controller 176 is operated to force a flow of the inflation fluid E through the conduits 172, 170T and into the balloon cavity 177, pressurize the inflation fluid E in the balloon cavity 177, and maintain the pressure of the inflation fluid E in the balloon cavity 177.

In a deflation operation or step, the dilation controller 176 is operated to draw a flow of the inflation fluid E out of the balloon cavity 177 through the conduits 172, 170T. The balloon 174 is thereby depressurized and deflated.

Figure 3:
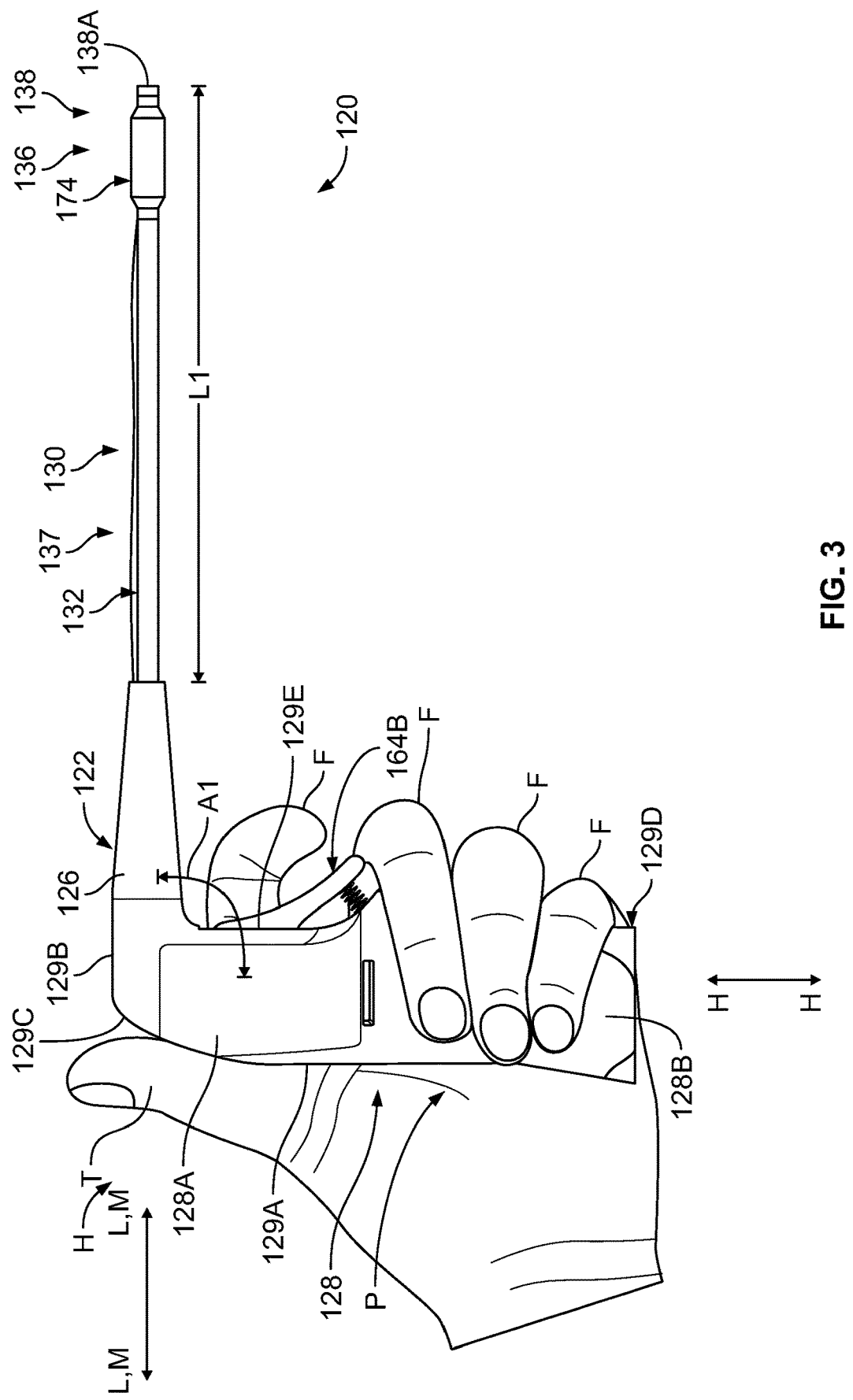
FIG. 3 is a side view of the instrument of FIG. 2.

With reference to FIGS. 1 and 3, the handle 128 and the faces 129A-F provide an ergonomic shape that can be gripped by an operator (e.g., physician) with one hand H like a handgun grip to position and navigate the probe 130 into, through and within the patient's anatomy. In use, the operator grasps the handle 128 such that the operator's palm P receives and bears against the rear face 129A while one or more of the operator's fingers F are positioned opposite the palm P and bear against the front faces 129D-F. Further, the operator may wrap his or her thumb T circumferentially around or alongside the handle 128, or may place the thumb T over the shoulder 129C and onto the top face 129B. One or more of the operator's fingers F can grasp the upper front face 129D while one or more of the operator's other (lower) fingers F grasp the lower front face 129E. One or more of the operator's fingers F can operate the trigger 164B as discussed below.

The ergonomic shape of the base 122 allows the handle to sit between the palm muscles and the opposing fingers providing an ergonomic solution to hold the handle by the operator. The device is further stabilized by positioning the thumb on to top of the handle. The ergonomic shape of the base 122 can thus provide the operator with improved dexterity, balance, and stability. The ergonomic shape of the base 122 enables the operator to effectively manipulate, position and operate the instrument 120 with a single hand holding the instrument 120.

The ergonomic shape also enables the operator to conveniently control aspiration via the instrument 120 using the trigger, as discussed herein. The trigger 164B is ergonomically located for displacement using the index and/or middle fingers.

In some embodiments, one or more control mechanisms (e.g., a button or switch) can be provided on the shoulder 129C or top face 129B. The design of the base 122 also enables the operator to conveniently and effectively access and actuate these mechanisms with the thumb of the single hand holding the base 122.

Typically, the probe 120 will be inserted into the patient through a nostril and guided to the target region of the patient's anatomy with the balloon 174 in its deflated configuration. Typically, during these steps, the light source 151 is activated in order to provide light for viewing the surgical field through the endoscope 20 and/or to provide trans-illumination through the patient's tissue. The operator can monitor the trans-illuminated light from external of the patient to identify the location of the probe tip 138A relative to the known anatomical features of the patient.

The probe 120 may be bent as described above prior to insertion of the probe 120 into the patient.

The irrigation system 165 can be used to flow or spray irrigation fluid onto the endoscope 20 to clean the lens 22 of the endoscope. Advantageously, the instrument 120 can be used in this manner to clean the endoscope 20 without requiring removal of the endoscope or the instrument 120 from the patient.

The sinus treatment system 10 and the instrument 120 may be used, in accordance with methods of the invention, to execute surgical and treatment procedures (e.g., balloon sinuplasty) using one or more of the operations or steps and functions described above. That is, for a given procedure, the operator can use the instrument 120 to aspirate, irrigate, deliver medication, dilate, and/or illuminate as described. Each of these operations or steps can be executed in a selected combination of operations or steps.

The aspiration, delivery, dilation, and/or illumination functions and operations can each be employed and executed independently of one another. Thus, for a given procedure, one or more of these operations can be omitted (i.e., the functionality is not used). One or more of the operations can be executed simultaneously. One or more of the operations can be executed sequentially.

Each of the operations of aspiration, delivery, dilation, and illumination can be executed without removing the probe 130 from the patient between different functions and without replacing a component in or on the probe. For example, it is not necessary to remove and reconfigure the probe 130 between steps of irrigating and aspirating. However, it may be necessary or desirable to remove the probe 130 from the patient in order to reconfigure the instrument 120 between the irrigation fluid delivery and medication delivery operations.

The illumination function of the instrument 120 can be used in combination with any of the function combinations or methods described below.

The aspiration function and operation can be used to suction fluid and/or debris from the surgical field (e.g., the paranasal sinuses). The fluid may include fluids that have been introduced to the surgical field by the operator (e.g., irrigation fluid and/or medication) or fluids or debris originating in the patient (e.g., mucus or blood). In this way, the suction function can be used to remove undesirable material (e.g., infectious or blocking material) and clear the field for visualization. For example, during the procedure, the suction function and operation can be used to remove bleeding from resultant mucosal trauma or ostial dilation that might otherwise obscure the endoscopic view of surgeon and thereby hamper the procedure.

In some procedures, the system 10 and instrument 120 are used as follows to dilate a portion of the patient's anatomy using balloon sinuplasty. The balloon 174 is maintained in the non-expanded configuration or placed in the non-expanded configuration using the inflation controller 176. With the balloon 174 deflated, the probe 130 is navigated into position in the patient anatomy (e.g., the paranasal sinuses). The balloon 174 is then inflated to the expanded configuration using the inflation controller 176 while in the selected position. The patient anatomy is thereby dilated and treated by the expansion of the balloon 174. Thereafter, the balloon 174 is deflated to the non-expanded configuration using the inflation controller 176, and removed from the patient. This dilation procedure may be supplemented with aspiration, delivery (irrigation fluid and/or medication), and illumination steps simultaneous with or in any selected sequence with the dilation steps.

In some procedures, the system 10 and instrument 120 are used to aspirate only, using the aspiration function.

In some procedures, the system 10 and instrument 120 are used to block or plug a passage of the patient anatomy with the expanded balloon 174, and then aspirate a region ("the plugged region") partially or fully sealed by the plugging of the passage, using the aspiration function. In some procedures, the plugged passage is an ostia or frontal recess, and the plugged region is a sinus adjacent and in fluid communication with ostia or frontal recess.

In some procedures, the system 10 and instrument 120 are used to expand the balloon 174 in a region of the patient anatomy while simultaneously aspirating using the aspiration function.

In some procedures, the system 10 and instrument 120 are used to irrigate only, using the irrigation delivery function.

In some procedures, the system 10 and instrument 120 are used to block or plug a passage of the patient anatomy with the expanded balloon 174, and then irrigate a region ("the plugged region") partially or fully sealed by the plugging of the passage, using the irrigation delivery function. In some procedures, the plugged passage is an ostia or frontal recess, and the plugged region is a sinus adjacent and in fluid communication with ostia or frontal recess.

In some procedures, the system 10 and instrument 120 are used to expand the balloon 174 in a region of the patient anatomy while simultaneously irrigating using the irrigation function.

In some procedures, the system 10 and instrument 120 are used to deliver medication only, using the medication delivery function.

In some procedures, the system 10 and instrument 120 are used to block or plug a passage of the patient anatomy with the expanded balloon 174, and then deliver medication to a region ("the plugged region") partially or fully sealed by the plugging of the passage, using the medication delivery function. In some procedures, the plugged passage is an ostia or frontal recess, and the plugged region is a sinus adjacent and in fluid communication with ostia or frontal recess In some procedures, the system 10 and instrument 120 are used to expand the balloon 174 in a region of the patient anatomy while simultaneously delivering medication using the irrigation function.

In some procedures, the system 10 and instrument 120 are used to irrigate, using the irrigation delivery function, and thereafter aspirate, using the aspiration function.

In some procedures, the system 10 and instrument 120 are used to block or plug a passage of the patient anatomy with the expanded balloon 174, then irrigate a region ("the plugged region") partially or fully sealed by the plugging of the passage, using the irrigation delivery function, and then aspirate the plugged region, using the aspiration function. The aspiration may remove the irrigation fluid from the plugged region. In some procedures, the plugged passage is an ostia or frontal recess, and the plugged region is a sinus adjacent and in fluid communication with ostia or frontal recess.

In some procedures, the system 10 and instrument 120 are used to block or plug a passage of the patient anatomy with the expanded balloon 174, then aspirate a region ("the plugged region") partially or fully sealed by the plugging of the passage, using the aspiration function, and then irrigate the plugged region, using the irrigation delivery function. The procedure may further include again aspirating the plugged region to remove the irrigation fluid, using the aspiration function. In some procedures, the plugged passage is an ostia or frontal recess, and the plugged region is a sinus adjacent and in fluid communication with ostia or frontal recess.

In some procedures, the system 10 and instrument 120 are used to aspirate, using the aspiration function, and irrigate, using the irrigation delivery function, simultaneously.

In some procedures, the system 10 and instrument 120 are used to plug a region of the patient anatomy with the expanded balloon 174, then aspirate and irrigate the plugged region simultaneously.

In some procedures, the system 10 and instrument 120 are used to block or plug a passage of the patient anatomy with the expanded balloon 174, then simultaneously aspirate and irrigate a region ("the plugged region") partially or fully sealed by the plugging of the passage, using the aspiration and irrigation functions. In some procedures, the plugged passage is an ostia or frontal recess, and the plugged region is a sinus adjacent and in fluid communication with ostia or frontal recess.

In some procedures, the system 10 and instrument 120 are used to deliver medication, using the medication delivery function, and thereafter aspirate, using the aspiration function.

In some procedures, the system 10 and instrument 120 are used to block or plug a passage of the patient anatomy with the expanded balloon 174, then deliver medication to a region ("the plugged region") partially or fully sealed by the plugging of the passage, using the delivery function, and then aspirate the plugged region. The aspiration may remove an excess of the medication from the plugged region, using the aspiration function. In some procedures, the plugged passage is an ostia or frontal recess, and the plugged region is a sinus adjacent and in fluid communication with ostia or frontal recess.

In some procedures, the system 10 and instrument 120 are used to aspirate, using the aspiration function, and thereafter deliver medication, using the medication delivery function. The procedure may further include again aspirating the plugged region to remove excess medication, using the aspiration function.

In some procedures, the system 10 and instrument 120 are used to block or plug a passage of the patient anatomy with the expanded balloon 174, then aspirate a region ("the plugged region") partially or fully sealed by the plugging of the passage, using the aspiration function, and then deliver medication to the plugged region, using the irrigation delivery function. The procedure may further include again aspirating the plugged region to remove excess medication, using the aspiration function. In some procedures, the plugged passage is an ostia or frontal recess, and the plugged region is a sinus adjacent and in fluid communication with ostia or frontal recess.

In some procedures, the system 10 and instrument 120 are used to aspirate, using the aspiration function, and deliver medication, using the medication delivery function, simultaneously.

In some procedures, the system 10 and instrument 120 are used to block or plug a passage of the patient anatomy with the expanded balloon 174, then simultaneously aspirate and deliver medication to a region ("the plugged region") partially or fully sealed by the plugging of the passage, using the aspiration and delivery functions. In some procedures, the plugged passage is an ostia or frontal recess, and the plugged region is a sinus adjacent and in fluid communication with ostia or frontal recess.

Each of the foregoing procedures may be further modified to include expanding the balloon 174 simultaneously with one or more of the aspiration and fluid delivery steps. The step of expanding the balloon to plug or modify the patient anatomy can be executed simultaneously or independently of the other steps or functions executed using the instrument 120 (i.e., aspiration, fluid delivery, and illumination).

Exemplary methods of use in accordance with some embodiments will now be described with reference to FIGS. 12A-12F.

The system 10 and balloon dilation catheter instrument 120 may be particularly suited for treatment of the sinus outflow tract.

FIG. 12A illustrates a cross-sectional (coronal) view of a maxillary sinus and other associated anatomical structures of a subject (i.e., a patient being treated).

FIG. 12A illustrates the cross-sectional (coronal) view of the maxillary sinus of the subject with the probe 130 of the instrument 120 (balloon dilation catheter) being advanced in the subject's nasal cavity toward a treatment target region.

FIG. 12B illustrates the cross-sectional (coronal) view of the maxillary sinus of the subject with the balloon 174 of the instrument 120 in a deflated or nonexpanded state and positioned in the maxillary ostia of the subject.

FIG. 12C illustrates the cross-sectional (coronal) view of the maxillary sinus of the subject with the balloon 174 of the instrument 120 being in an inflated or expanded state in the maxillary ostia of the subject. The balloon 174 has been inflated using the dilating system 170.

FIG. 12D illustrates the cross-sectional (coronal) view of the maxillary sinus of the subject with the balloon 174 of the instrument 120 being in an inflated or expanded state in the maxillary ostia of the subject and the maxillary sinus being irrigated and suctioned at the same time using the aspiration system 160 and the delivery system 165. By keeping the balloon 174 inflated during this process, there is very little excursion of fluid out of the maxillary ostia and into the nasal cavity and nasopharynx. This allows substantially all of the irrigated fluid to be suctioned back out of the maxillary sinus.

FIG. 12E illustrates the cross-sectional (coronal) view of the maxillary sinus of the subject with the balloon 174 of the instrument 120 being in an inflated or expanded state in the maxillary ostia of the subject and medications being applied to the maxillary sinus using the delivery system 165. By keeping the balloon 174 inflated during this process there is little to no excursion of medications out of the maxillary sinus.

Figure 12F:
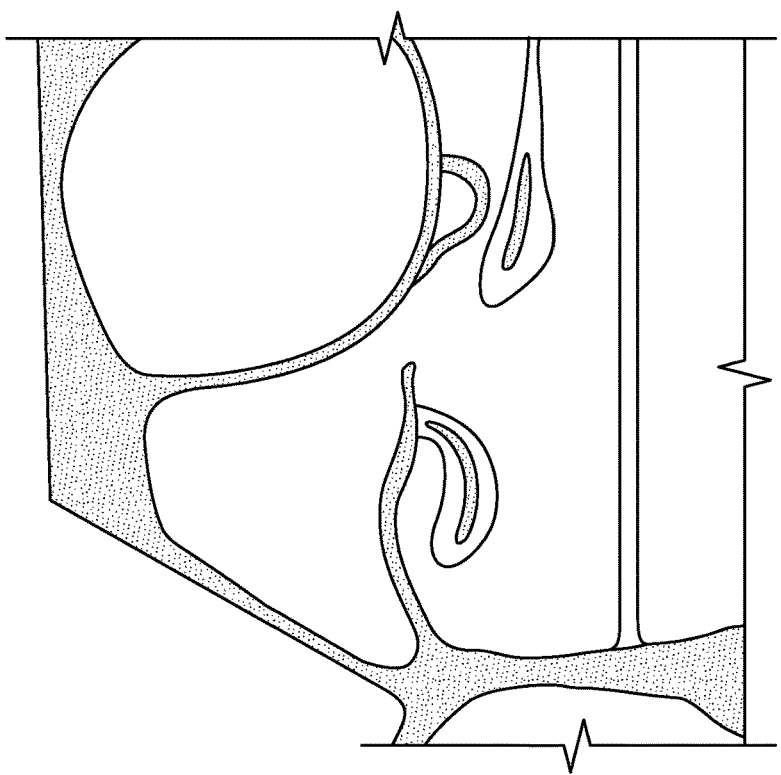

FIG. 12F illustrates cross-sectional (coronal) view of a dilated maxillary ostia of the subject after a balloon dilation procedure using the balloon 174.

Figure 13A:
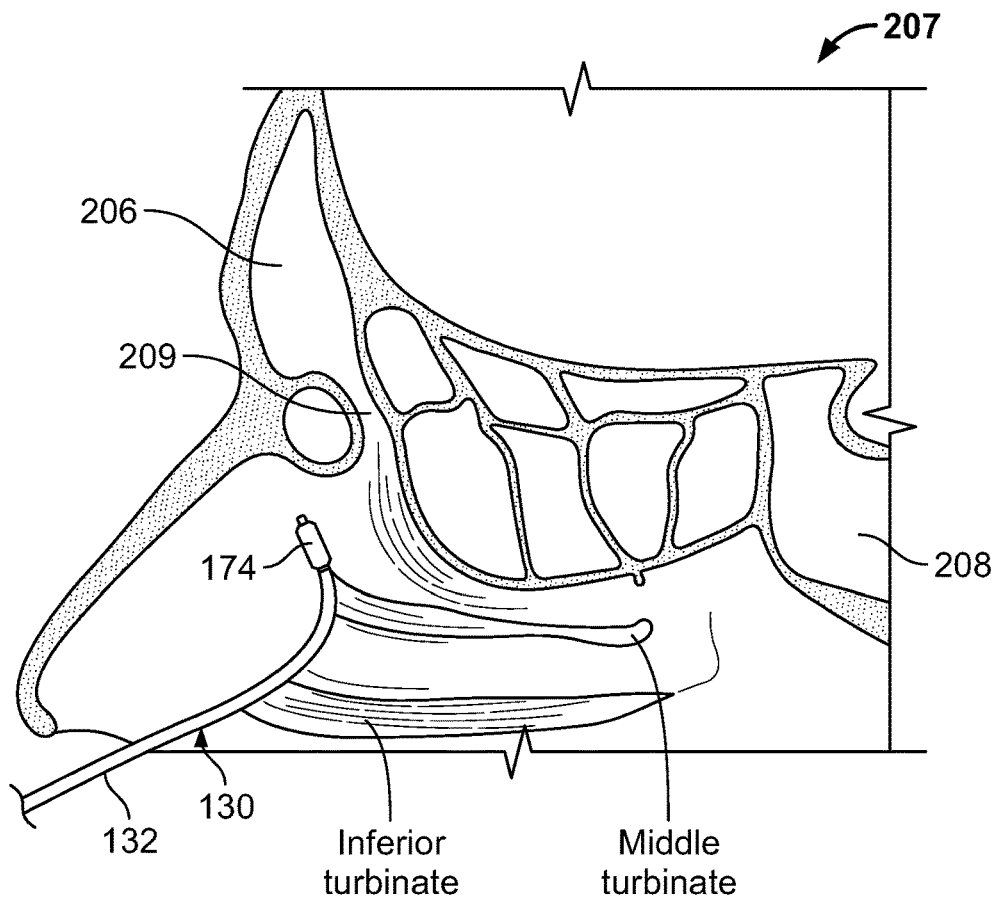

FIG. 13A illustrates the cross-sectional (sagittal) view of the frontal sinus and other associated anatomical structures of a subject (i.e., a patient being treated).

FIG. 13A illustrates the cross-sectional (sagittal) view of the frontal sinus of the subject with the probe 130 of the instrument 120 being advanced in the subject's nasal cavity towards the frontal recess.

Figure 13B:
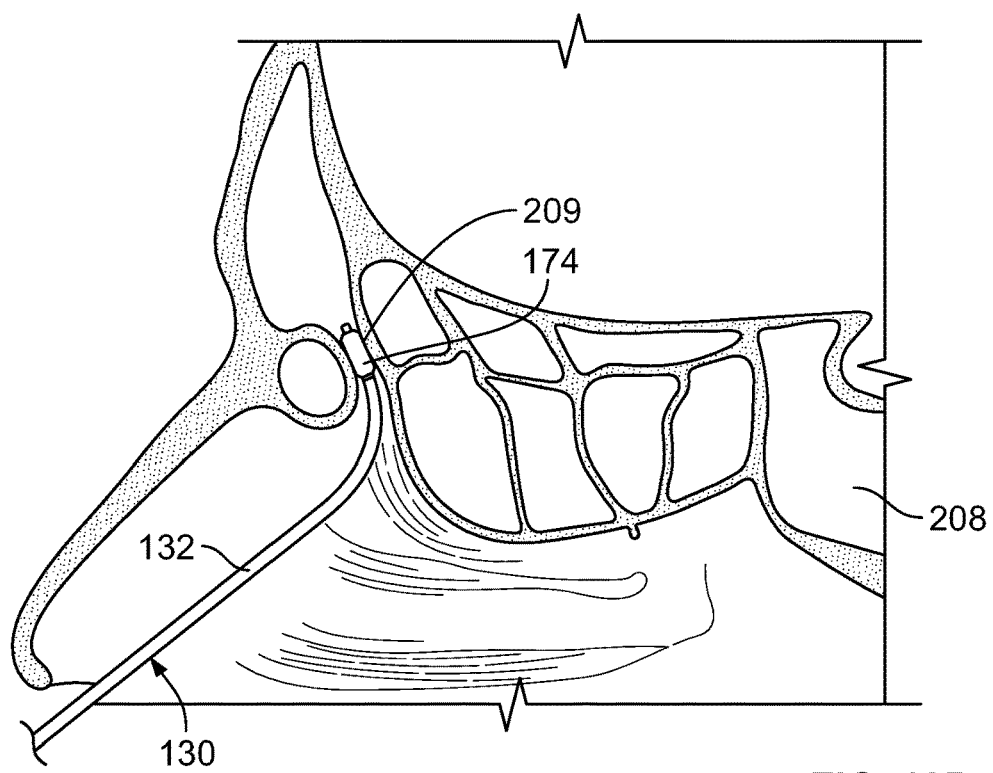

FIG. 13B illustrates the cross-sectional (sagittal) view of the frontal sinus of the subject with the balloon 174 of the instrument 120 in a deflated or nonexpanded state and positioned in the frontal recess of the subject.

Figure 13C:
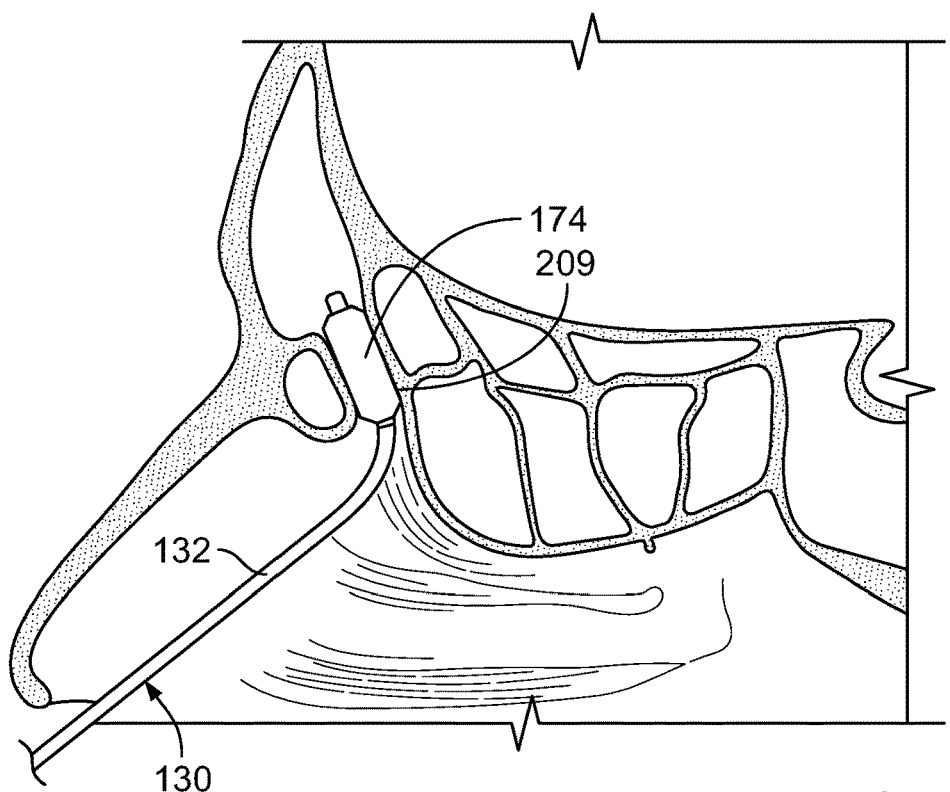

FIG. 13C illustrates the cross-sectional (sagittal) view of the frontal sinus of the subject with the balloon 174 of the instrument 120 being in an inflated or expanded state in the frontal recess of the subject.

Figure 13D:
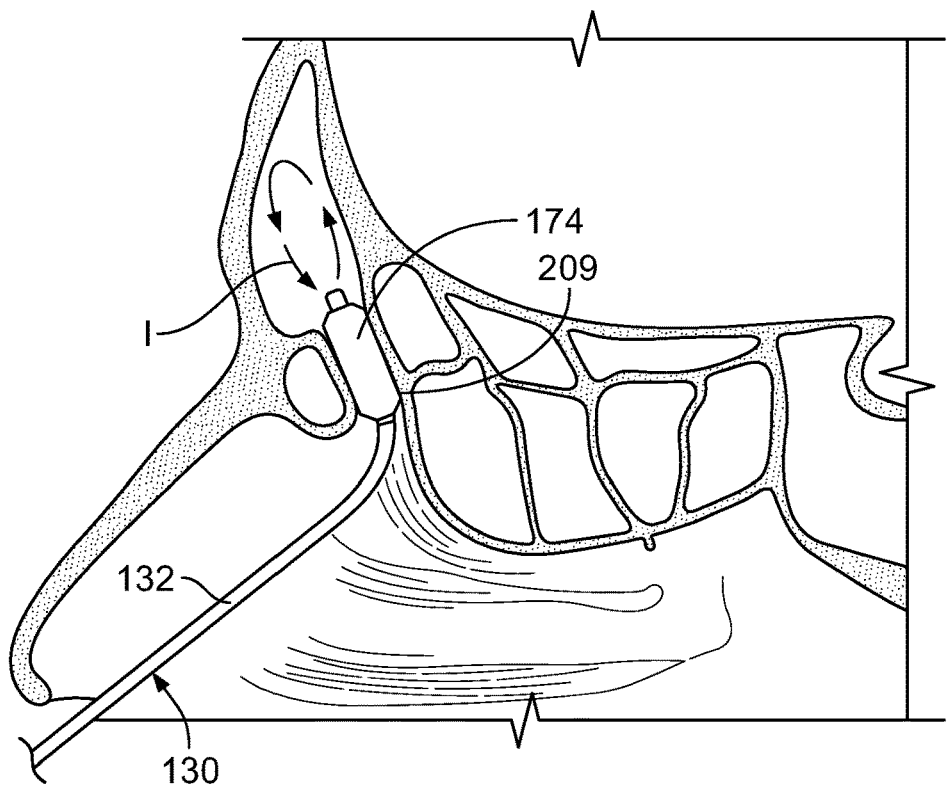

FIG. 13D illustrates the cross-sectional (sagittal) view of the maxillary sinus of a subject with the balloon 174 of the instrument 120 being in an inflated or expanded state in the frontal recess of the subject and the frontal sinus being irrigated and suctioned at the same time using the aspiration system 160 and the delivery system 165. By keeping the balloon inflated during this process there is very little excursion of fluid out of the frontal recess and into the nasal cavity and nasopharynx. This allows all the irrigated fluid to be suctioned back out of the frontal sinus.

Figure 13E:
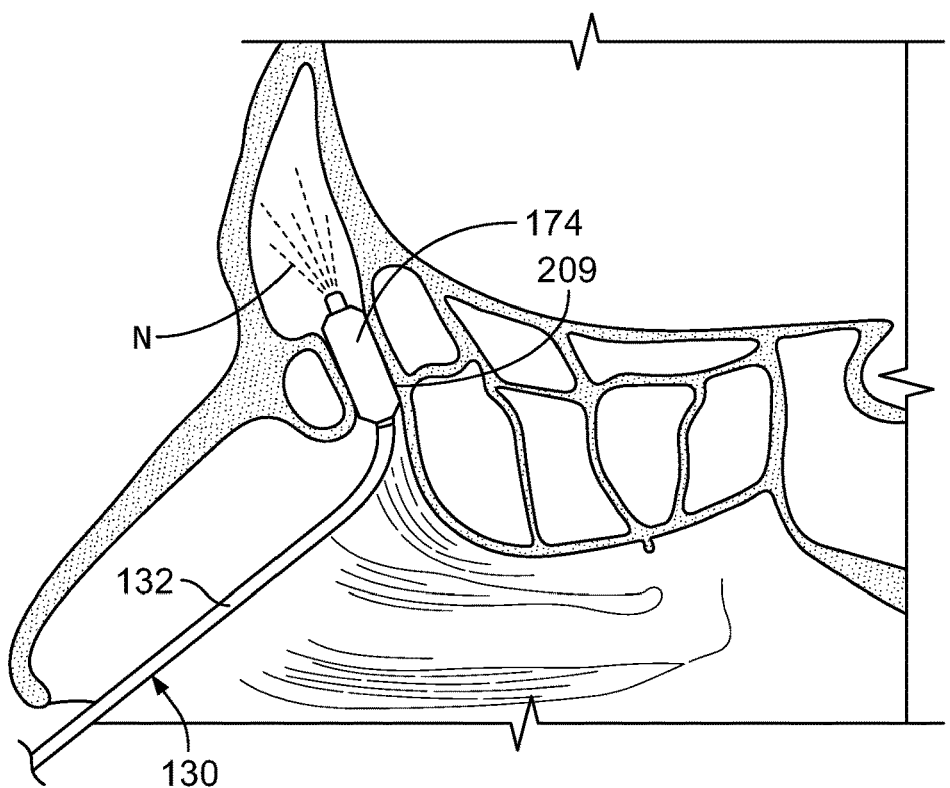

FIG. 13E illustrates the cross-sectional (sagittal) view of the frontal sinus of a subject with the balloon 174 of the instrument 120 being in an inflated or expanded state in the frontal recess of the subject and medications being applied to the frontal sinus using the delivery system 165. By keeping the balloon inflated during this process there is little to no excursion of medications out of the frontal sinus.

Figure 13F:
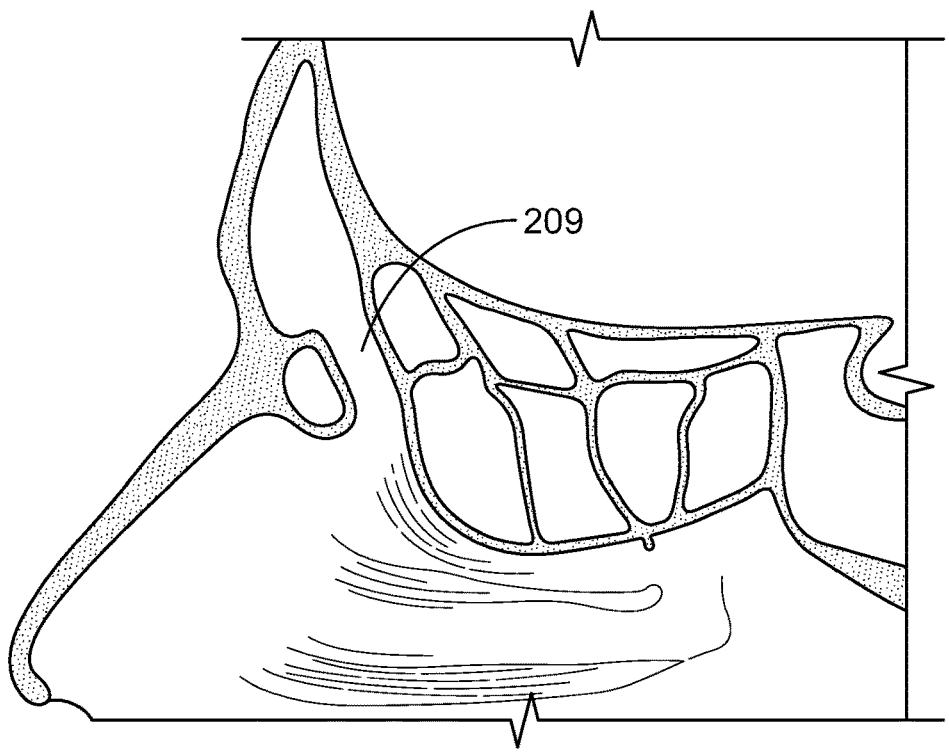

FIG. 13F illustrates cross-sectional (sagittal) view of a dilated frontal recess after balloon dilation procedure using the balloon 174.

During use, the probe 130 is manipulated and advanced across or into the anatomical space of interest. As shown in FIGS. 12A, 12B, 13A and 13B, the balloon 174 is typically in a deflated state during the time that the probe 130 is being moved or navigated into position and when the instrument 120 is being used for steps not requiring an expanded balloon 174. After the probe 130 is properly positioned in the sinus ostia or sinus outflow pathways, the balloon 174 is inflated.

During the procedure, any bleeding from resultant mucosal trauma or ostial dilation can obscure the endoscopic view of surgeon thereby hampering the procedure. The system 100, instrument 120 and methods of the present invention provide a mechanism to suction out the mucus present in the sinus as well as a mechanism to irrigate the diseased sinus, and the capability to execute both activities simultaneously or independently, as desired.

Unlike known devices that are designed to be held like a pen between the operating surgeons thumb and forefinger with the device resting in the interdigital space between the thumb and forefinger, the instrument 120 employs a more ergonomic design. The ergonomic design of the instrument 120 places the dominant loads of the instrument in line with the weight bearing muscles of the operator's arm. This reduces undue weight pressure on the surgeon's forearm and wrist, which can reduce or prevent wrist cramps as compared to "pen" type devices. In addition, the ergonomic design of the instrument 120 extends the range of motion of the operator.

Using a probe 130 made up of rigid but malleable material enables the balloon dilation catheter 120 to be positioned without the need of a separate guiding catheter or guide wire in most, if not all, instances.

Having a suction or aspiration functionality permits the removal of blood and other secretions which makes it easier to visualize the placement of the balloon dilation catheter 120 during the procedure done using an endoscope.

The suction or aspiration system 160 may be used for suction or aspiration of blood or other secretions. The delivery system 165 may be used for delivery of fluids and/or medicaments to the sino-nasal cavity. By providing separate, coexisting conduits for suction and delivery, respectively, in the instrument 120 and the probe 130, the instrument enables simultaneous suction and irrigation. This can prevent the flooding of the operating field by the irrigation fluid. In addition, thick secretions can be diluted by irrigating and made dilute enough to be suctioned/aspiration in the suction conduit. This keeps the endoscopic view of the operating field clear and allows for clear visualization of the anatomy.

The different shapes of the probe 130 may be factory-formed in a particular shape and offered as a different model as fully assembled. Alternatively, the probe 130 may be one of a set of replaceable, interchangeable or modular elements that can mounted inside the handle 128 using a slide and press-it type sealing arrangement. In yet another alternative, the shapes of the probe 130 could represent desirable shapes that a malleable inner guide member could be formed into by the user to better fit a particular application or subject's anatomy.

Light emitted from the distal end of the waveguide 154 at the distal end of the probe 130 can be used to guide for the proper placement of the probe 130. In particular, the light can provide trans-illumination through the tissue of the patient, which the surgeon can observe and use to ascertain the location of the tip 138A relative to the patient's anatomy.

Also, the light emitted from the distal end of the waveguide 154 can help illuminate the surgical field for view through the endoscope 20.

Figure 14:
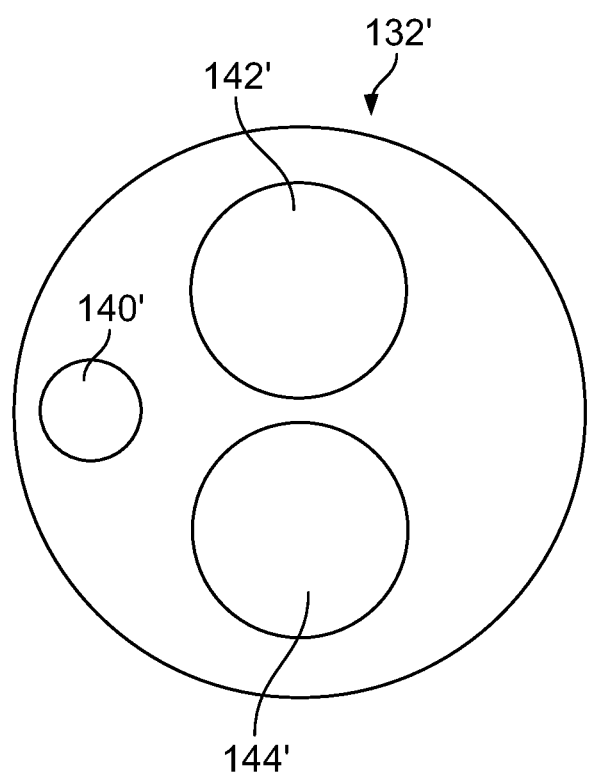
FIG. 14 is a distal end view of a shaft according to alternative embodiments.
Figure 15:
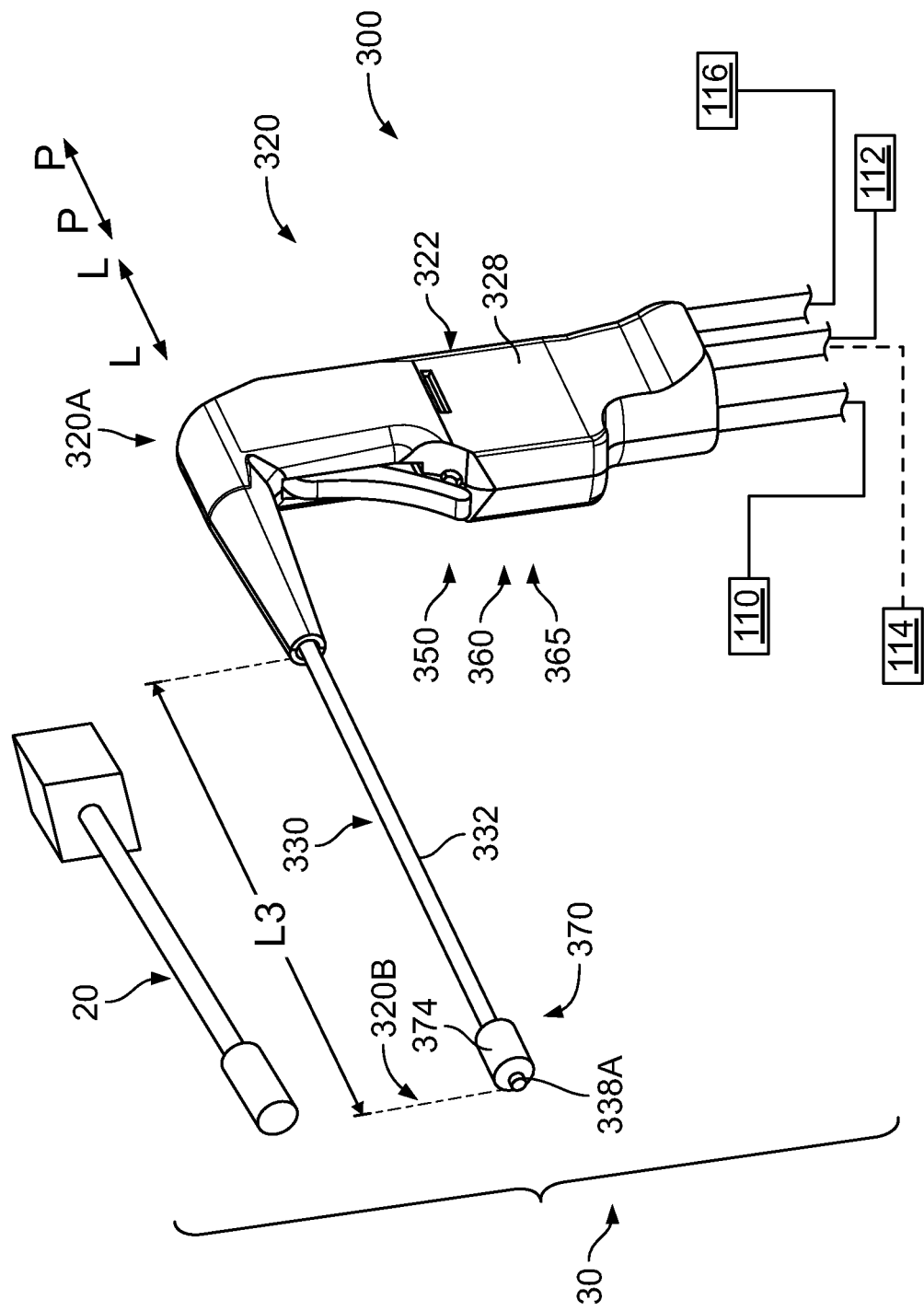
FIG. 15 is front perspective, schematic view of a sinus treatment system according to further embodiments.
Figure 16:
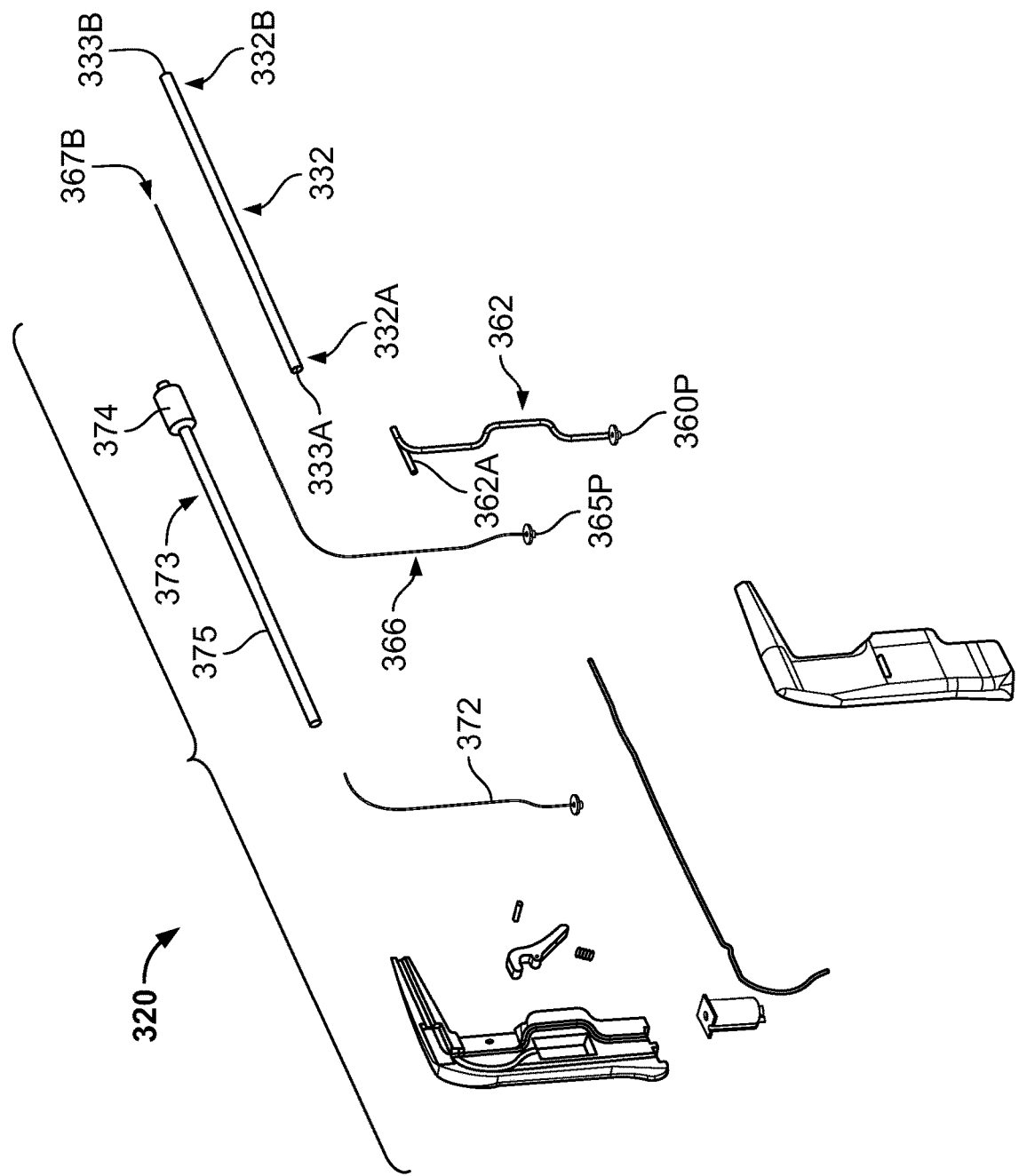
FIG. 16 is an exploded, rear perspective view of an instrument forming a part of the sinus treatment system of FIG. 15.
Figure 17:
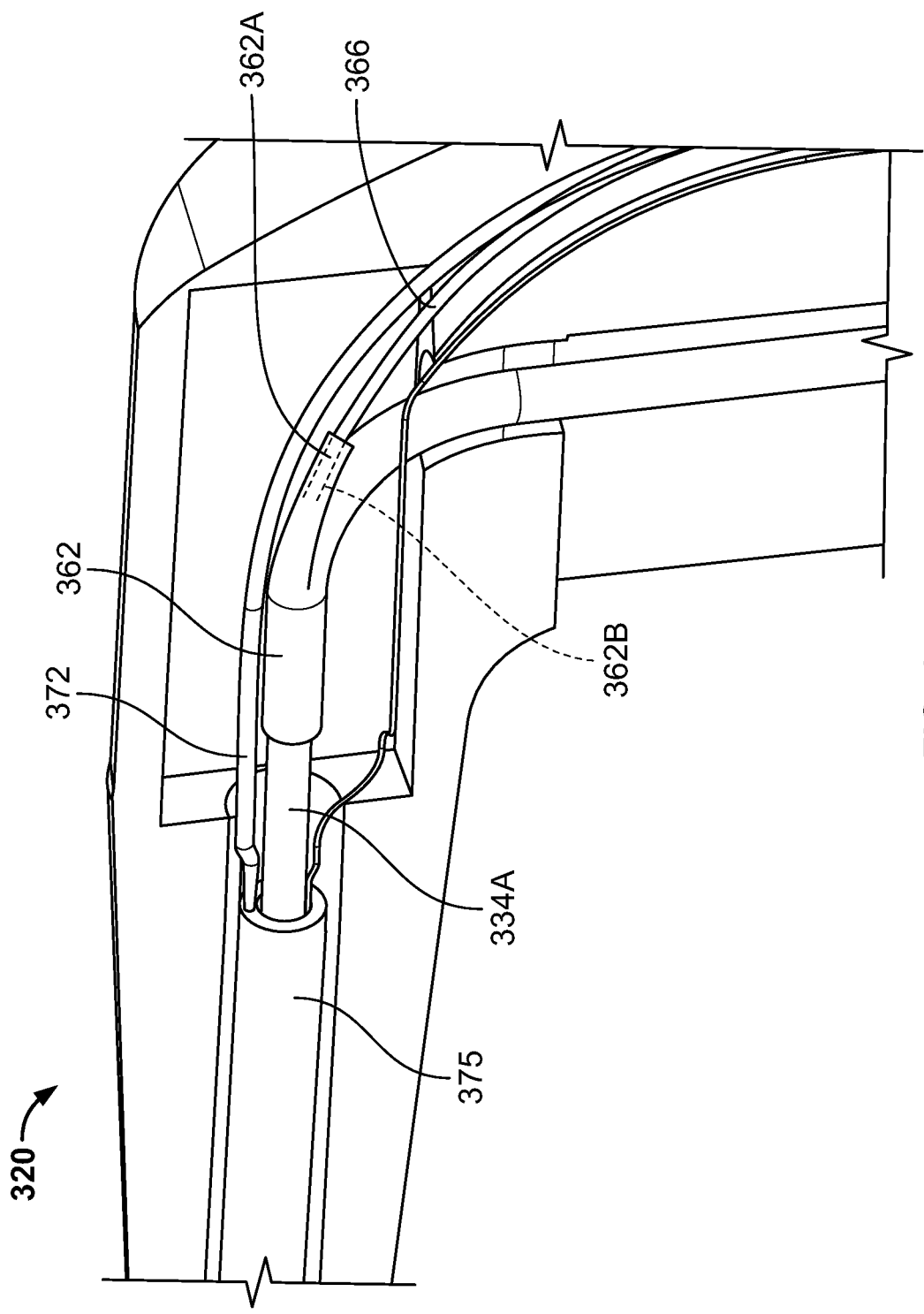
FIG. 17 is a fragmentary, rear perspective view of the instrument of FIG. 16.

In other embodiments, the shaft 132 may include aspiration, delivery, and waveguide lumens of different cross-section shapes than those illustrated for the lumens 140, 142, 144. For example, FIG. 14 shows an alternative shaft 132' including a waveguide lumen 140', an aspiration lumen 142, and an irrigation lumen 144.

In other embodiments, the inflation conduit 172 may be replaced with a tubular sheath that surrounds the shaft 132 and forms an inflation channel in the space between the sheath and the outer diameter of the shaft 132. In this case, the sheath may be substantially non-expandable or relatively non-expandable compared to the balloon 174.

In further embodiments, the inflation conduit 172 and the balloon 174 may be replaced with a self-sealed balloon member as described below with regard to the balloon member 373.

With reference to FIGS. 15-21, a sinus treatment system 30 according to further embodiments of the invention is shown therein. The system 30 includes sinus treatment instrument system 300 and, optionally, an endoscope 20. The system 30 and the instrument system 300 can be used in the same manner as the system 10 and the instrument system 100. However, the instrument system 300 is differently constructed than the instrument system 100.

The instrument subsystem 300 includes a handheld instrument 120, the suction (negative pressure or vacuum) source 110, the irrigation fluid source 112, the medication source 114, and the inflation fluid source 116.

The instrument 320 is a balloon dilation catheter device that includes the same functional features and mechanisms in addition to the dilation functionality as described for the instrument 100. The instrument 120 includes a handheld unit or base 322, a probe (or guide member or extension assembly) 330, a lighting system 350, an aspiration system 360, a delivery system 365, and a dilation system 370 constructed and operative in the same manner as the base 122, the probe 130, the lighting system 150, the aspiration system 160, the delivery system 165, and the dilation system 170, except as discussed below. The instrument 320 has a proximal end 320A and a distal end 320B defining a primary or longitudinal axis L-L.

The probe 130 includes an elongate, tubular shaft 332 defining a longitudinal probe axis P-P extending from a proximal end 332A to a distal end 332B. The probe axis P-P is substantially parallel to the instrument axis L-L. The shaft 332 includes a dilator section 336, an intermediate section 337, and a tip section 338. The tip section 338 terminates at a tip 338A.

The shaft 332 has an outer surface 334A and an inner surface 334B. In some embodiments, the outer and inner surfaces 334A, 334B are substantially cylindrical. The inner surface 334B defines an axially extending shaft passage or lumen 333. The shaft lumen 333 extends fully from a proximal end opening 333A in the end 332A to a distal end opening 333B in the end 332B.

The shaft 332 may be formed of any suitable material(s). In some embodiments, the shaft 332 is formed of a stainless steel hypotube.

In some embodiments, the shaft 332 is unitary. In some embodiments, the shaft 332 is unitarily formed. In some embodiments, the shaft 332 is monolithic. The shaft 332 may be molded (e.g., injection molded) or extruded.

In some embodiments, the shaft 332 is formed of a rigid but malleable material. This permits the shaft 332 to be deliberately bent into a new shape or configuration in response to application of a sufficient bending force, and to retain the original or new shape or configuration when a lesser force is applied to the shaft 332. In some embodiments, the required bending force is greater than any force the shaft 332 is expected or intended to experience in service during the surgical procedure (i.e., during navigation or use of the probe 320 within the anatomy of the patient). The malleability of the shaft 332 may enable the user to bend the shaft 332 into a desired angle or curvature to achieve proper positioning for the balloon 374 and the distal end tip 338A in the sinus ostia or sinus drainage pathways.

In some embodiments, the shaft 332 is pre-shaped to have a curved distal portion. The curved distal portion may be configured to match with the frontal sinus outflow tract or frontal recess.

In some embodiments, the distal portion the shaft 332 is formed right to the distal end 332B and may have a radius of curvature in the range of from about 0.25 inch to about 1.5 inch and, in some embodiments, from about 0.75 to about 1.25 inch.

The shaft 332 extends a predetermined or prescribed distance or length L3 (FIG. 15) from the base 322 to the distal end 332B. In some embodiments, the length L3 is in the range of from about 3 to 10 inches and, in some embodiments, from about 5 to 7 inches.

In some embodiments, the probe 330 has an outer diameter in the range of from about 1 to 5 mm and, in some embodiments, from about 3 to 7 mm.

In some embodiments, the shaft 332 has a nominal wall thickness T3 (FIG. 19) in the range of from about 0.1 to 0.3 mm and, in some embodiments, from about 0.2 to 0.5 mm.

In some embodiments, the distal tip 338A has an outer diameter in the range of from about 1 to 3 mm and, in some embodiments, from about 2 to 5 mm.

In some embodiments, the edges of the tip 338A are rounded or smooth to prevent or reduce trauma to the mucosa of the sinuses.

The aspiration system 360 includes an aspiration conduit 362 in place of the conduit 162. The conduit 362 extends through the handle 328. A proximal end of the conduit 362 is fluidly connected to the suction port 360P. The distal end of the conduit 362 is fluidly coupled to the proximal opening 333A of the shaft lumen 333, and thereby to an annular aspiration lumen 363 as discussed below. The conduit 362 further includes an integral, tubular tap or receiver leg 362A. A receiver port 362B is defined in the leg 362A and is also fluidly connected to the proximal opening 333A.

The aspiration conduit 362 may be formed of any suitable material. In some embodiments, the conduit 362 is formed of an elastomeric material. In some embodiments, the conduit 362 is formed of a flexible material. Suitable materials for the conduit 362 may include silicone, for example.

The delivery system 365 includes a conduit 366. The conduit 366 defines a longitudinally extending delivery lumen 367 that terminates at a distal end opening 367B.

The delivery conduit 366 extends from the delivery port 365P, through the handle 328, through the receiver port 362B, through the distal portion of the conduit 362, through the shaft lumen 333, and the distal end 332B. In some embodiments, the terminal end and distal end opening 367B of the delivery conduit 366 are located substantially at the distal end opening 333B.

In some embodiments, a fluid-tight seal is provided between the conduit 366 and the conduit 362 at the port 362B.

The delivery conduit 366 may be formed of any suitable material. In some embodiments, the conduit 366 is formed of an elastomeric material. In some embodiments, the conduit 366 is formed of a flexible material. Suitable materials for the conduit 366 may include silicone, for example.

The dilation system 370 includes a balloon member 373 in place of the conduit 172 and the balloon 174. The balloon member 373 is a self-sealed balloon unit. The balloon member 373 includes a conduit 372, an integral dilation section 374, and an integral nondilation section 375.

The dilation section 374 is a balloon. The balloon 174 is donut-shaped and includes a tubular inner wall 374A and a tubular outer wall 374B defining an enclosed, annular balloon chamber 374C radially therebetween.

The nondilation section 375 includes a tubular inner wall 375A and a tubular outer wall 375B defining an enclosed, annular inflation passage 375C radially therebetween. The passage 375C fluidly connects the conduit 372 to the balloon chamber 374C.

The balloon 374 is mounted proximate the distal end 332B. The balloon member 373 may be bonded to the shaft 332 using a weld, adhesive, or the like. Alternatively, the balloon 374 may be secured to the shaft 332 using a mechanical connection.

The dilation system 370 is configured to selectively inflate and deflate the balloon 374 on demand by the operator as described above for the balloon 174. The balloon 374 is pliable and expandable when inflated. The dilation system 170 can be operated to place the balloon 374 alternatively in at least a first, relatively radially non-expanded configuration (herein, the non-expanded position) and a second, radially expanded configuration (herein, the expanded configuration). In the expanded configuration, the outer diameter D4 (FIG. 18) of the balloon 374 is larger than in the deflated configuration.

The nondilation section 375 is non-expandable or less expandable than the balloon 374 so that, when the balloon 374 is inflated and expanded, the nondilation section 375 will not radially expand or will expand to a substantially lesser extent than the balloon 374.

In some embodiments and as will be appreciated from the description herein, the dilation system 370 can be operated to place the balloon 374 in a range of different expanded configurations. That is, the balloon 374 can be forced to assume one of a plurality of different expanded configurations each having a different outer diameter D4.

In some embodiments and as will be appreciated from the description herein, the non-expanded configuration of the balloon 374 may not be a fully non-expanded or deflated configuration. That is, the outer diameter of the balloon 374 may be greater than is smallest possible diameter in the non-expanded configuration.

In some embodiments, the main section 374A takes on a cylindrical frusto-conical shape when the balloon 374 is substantially fully inflated.

In some embodiments, the balloon 374 has dimensions as described above for the balloon 174.

The balloon 374 may be formed of any suitable material. In some embodiments, the balloon 374 is formed of a material and/or using a technique as described above for the balloon 174.

Figure 18:
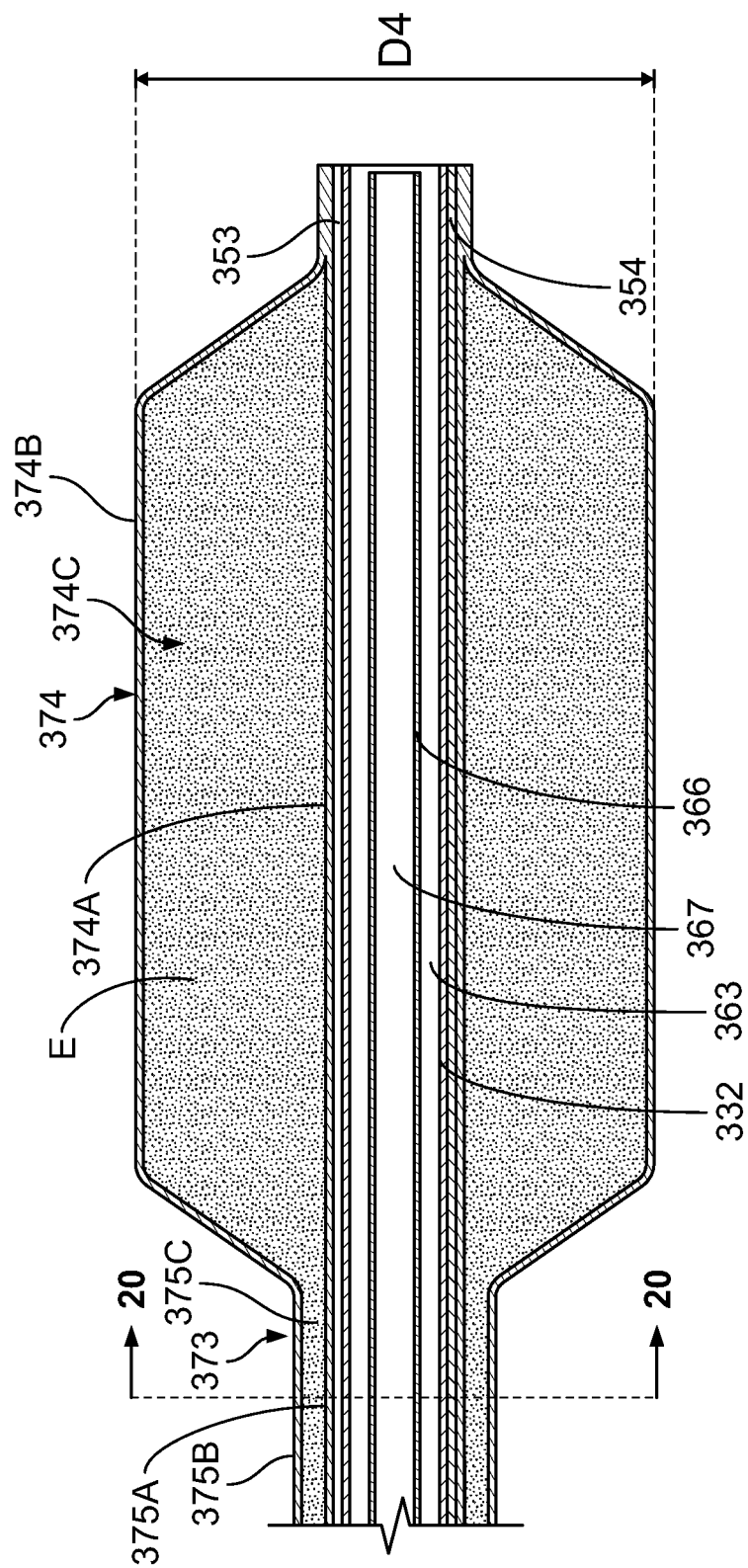
FIG. 18 is a cross-sectional view of the instrument of FIG. 16, wherein a balloon forming a part of the instrument is in an expanded position.
Figure 19:
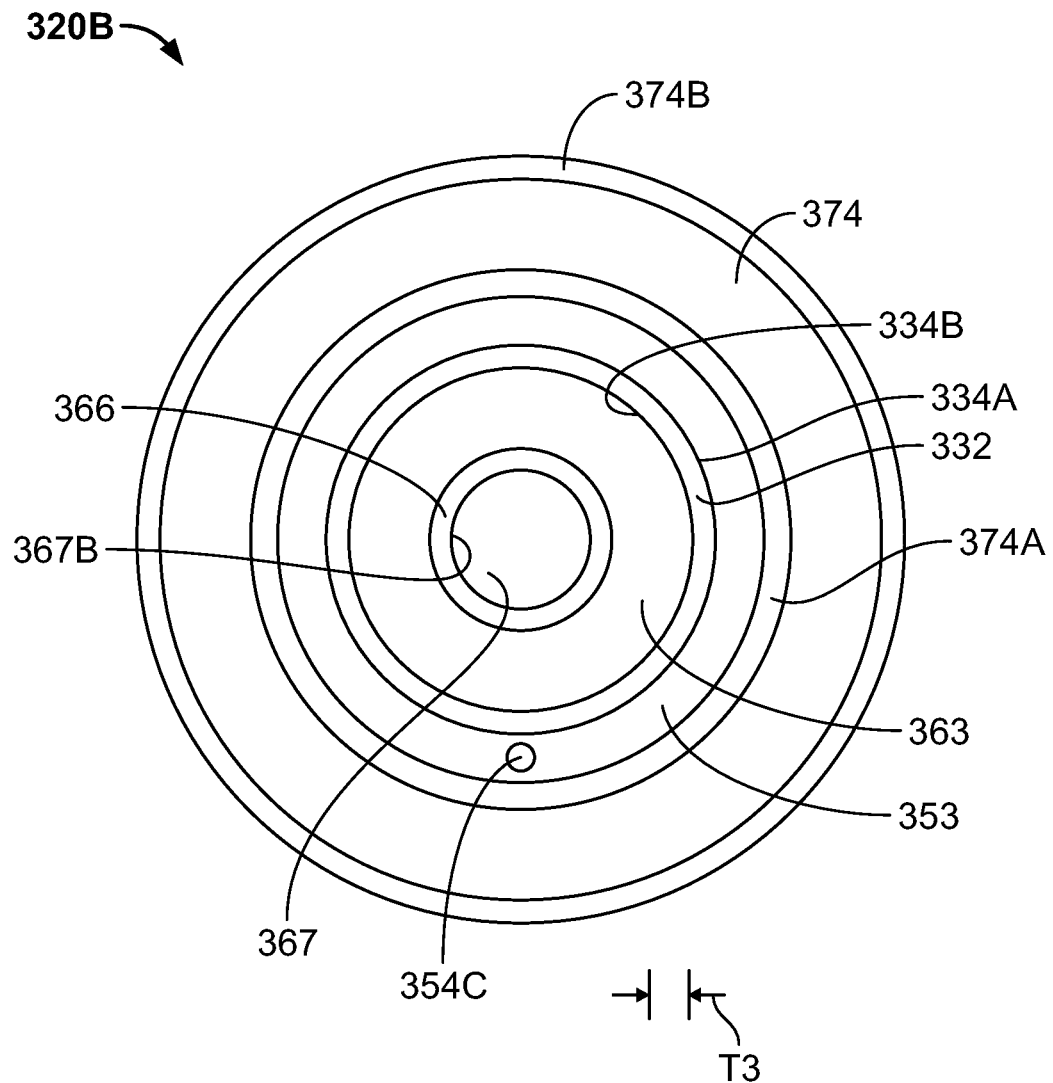
FIG. 19 is a distal end view of the instrument of FIG. 16.
Figure 20:
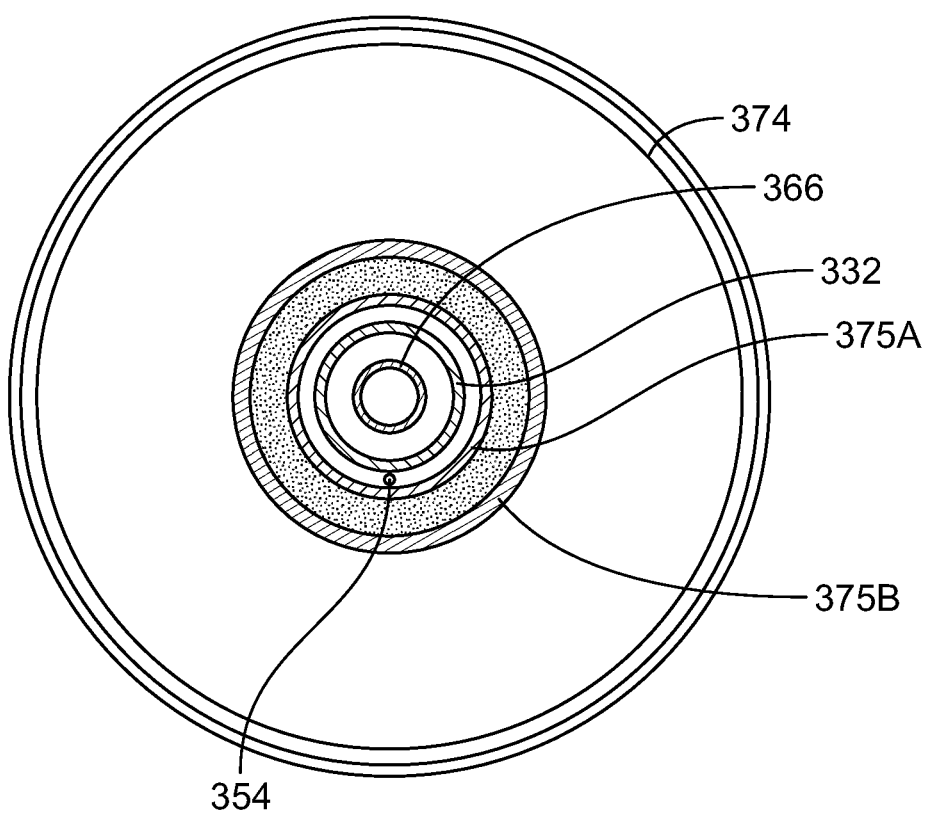
FIG. 20 is a cross-sectional view of the instrument of FIG. 16 taken along the line 20-20 of FIG. 18.
Figure 21:
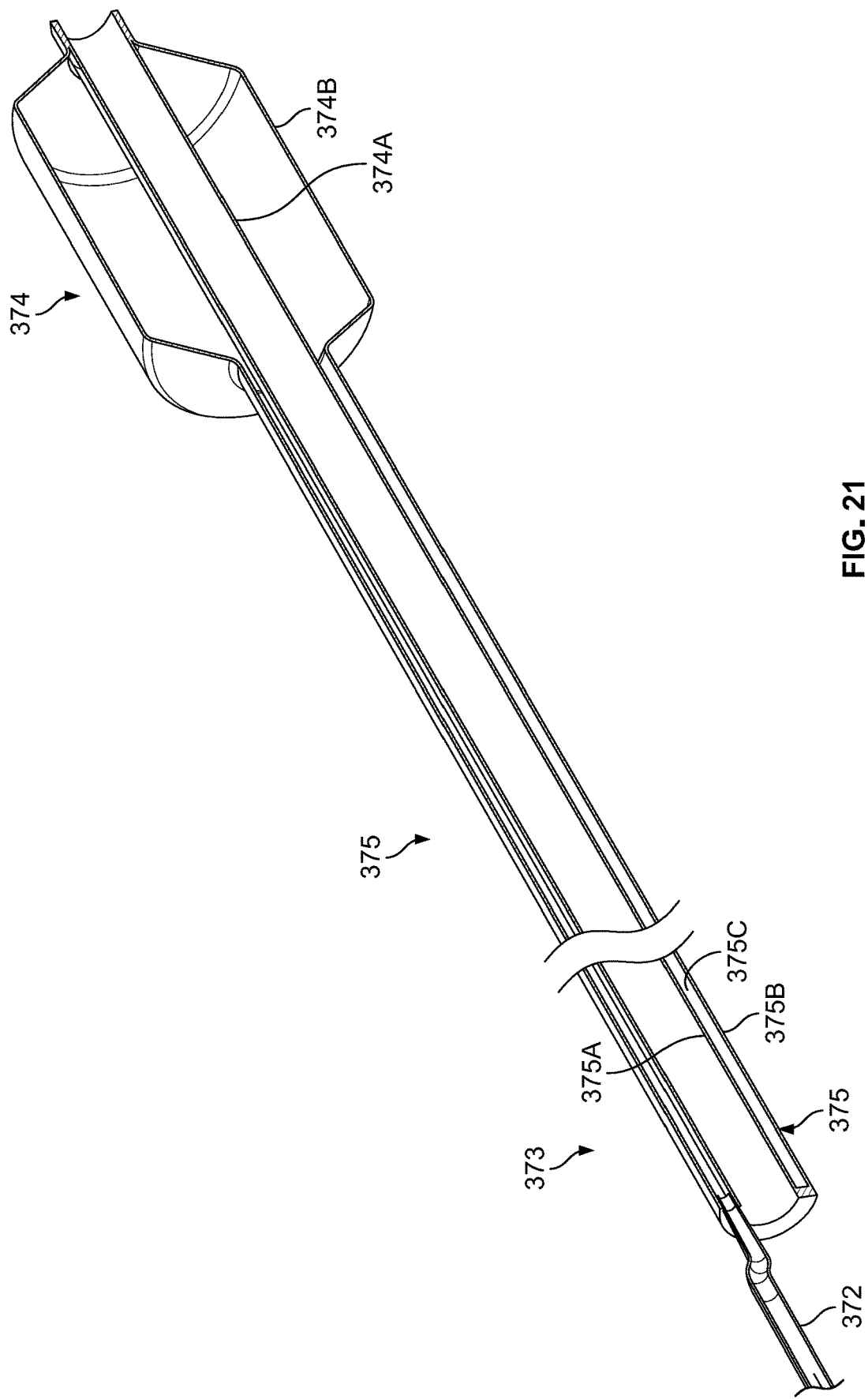
FIG. 21 is a fragmentary, rear perspective view of a balloon member forming a part of the instrument of FIG. 16.

As shown in FIGS. 18 and 19, a longitudinally extending space 353 is defined between the outer surface 334A of the shaft 332 and the inner wall 374A of the balloon member 373.

The integral lighting system 350 includes a waveguide 354 constructed and operative in the same manner as the waveguide 154. In some embodiments, the waveguide 354 is an optical fiber (e.g., a polymeric or glass optical fiber) and may include a sheath to protect the waveguide and prevent light loss. The waveguide 354 extends from the light source 351 and longitudinally through the space 353 to a waveguide distal end 354B adjacent the shaft distal end 332B. The waveguide 354 has an end face 354C at the distal end 354B, from which light is emitted. In some embodiments, the waveguide distal end 354B is located substantially flush with the distal end 332B. In other embodiments, the waveguide distal end 354B extends outwardly beyond the distal end 332B a distance in the range of from about 1 to 5 cm.

It can be seen in FIG. 19 that the shaft 332 and the delivery conduit 366 nested therein define generally concentric aspiration and delivery lumens. In particular, the delivery conduit 366 defines an inner or generally central delivery lumen 367. The shaft 332 and the delivery conduit 366 define the annular aspiration lumen radially surrounding but fluidly partitioned or separated from the delivery lumen 367.

In some embodiments and as shown in FIG. 19, the lumens 363 and 367 may have different cross-sectional areas from one another. In some embodiments, the cross-sectional area of the aspiration lumen 363 is greater than the cross-sectional area of the delivery lumen 367. In some embodiments, the cross-sectional area of the aspiration lumen 363 is at least 1.5 times the cross-sectional area of the delivery lumen 367. In some embodiments, the cross-sectional area of the aspiration lumen 363 is in the range of from about 2 to 4 times the cross-sectional area of the delivery lumen 367.

In some embodiments, the cross-sectional area of the aspiration lumen 363 is in the range of from about 0.28 to 1.75 mm$^2$.

In some embodiments, the cross-sectional area of the delivery lumen 367 is in the range of from about 0.07 to 0.8 mm$^2$.

In alternative embodiments, the instrument 320 is modified so that the inner lumen 367 is used to aspirate and the outer lumen 363 is used to deliver fluids (e.g., irrigation fluid and/or medication).

Balloon inflation devices and methods according to embodiments of the invention can be used for the treatment of diseased paranasal sinuses. More particularly, embodiments can provide minimally invasive, balloon based systems and methods for dilating the sinus ostium or drainage pathways of human paranasal sinuses in the treatment of chronic rhinosinusitis and other related disorders.

In some embodiments, a balloon dilation device includes a handle shaped like a gun holder, a rigid shaft that is coupled to an expandable balloon, a rigid shaft with tubing system to simultaneously suction, irrigate, and/or deliver medication to surgically dilate the anatomically stenotic segments of the paranasal sinuses (namely: maxillary, frontal and sphenoid sinus) by placing the balloon in the ostia and drainage pathways of the sinuses. The balloon is inflated to expand or remodel the drainage pathway.

In some embodiments, a device is provided for balloon dilation of anatomically stenotic segments of the paranasal sinuses in humans, for delivering medications to the paranasal sinuses and for collecting fluid or tissue specimens from the paranasal sinuses for diagnostic purposes. A device for dilating an ostium of a paranasal sinuses may include: a handle in a shape that utilizes the palm of the hand and apposition fingers to stabilize the device; an elongate shaft that is easily moldable having a proximal end coupled with the handle and extending to a distal end; a dilator balloon mounted on the shaft and having a non-expanded configuration and an expanded configuration.

In some embodiments, a device includes an ergonomically designed handle piece, a rigid probe coupled to an inflatable balloon on an outside surface of the probe, and a system of tubes on the inside of the probe to carry fiber optic from a light source housed in the handle piece, and a system of tubing and valves that allow for simultaneous suction and irrigation independent of the inflation status of the balloon. The handle piece may be configured to be held by the operating surgeon in his palm whereby the handle sits between the muscles of the palm and is opposed by the four fingers with the index finger controlling a suction trigger. The handle piece is further stabilized by the thumb from the top. This results in distribution of the weight of the system in line with the axis of the muscles of the arm. The rigid probe can be bent at various angles to navigate the sino-nasal passageways and helps in positioning the balloon at the correct location. Curvature and longitudinal location of the curved segment is configured by the operating surgeon.

In some embodiments, the balloon 174 is coated with one or more medicaments at one or more predetermined locations along the length of the balloon 174. This enables the delivery of medicaments to the area or the sinuses dilated by the balloon 174.

Because the sizes of the sinus openings and the depths of the sinuses are different for maxillary/frontal/sphenoid sinuses resulting in different portions of the balloon 174 being in contact with maxillary, frontal and sphenoid sinus openings, respectively, the balloon 174 may be coated with medicaments at three different locations on the balloon 174, and these medicaments can be transferred to the respective sinus openings.

It will be appreciated that the system 10 may include items such as a vacuum pump, reservoirs for dispensing and collecting fluids, a power supply, pumps, hydraulic cylinders, pressure sensors, flow control valves, and/or electronic controls as parts of or supplemental to the suction source 110, the irrigation fluid source 112, the medication source 114, the aspiration system 160, the delivery system 165, and the dilation system 170.

In some embodiments, the Luer lock connectors of the ports 160P, 165P, 170P are recessed into the profile of the handle 128.

According to further embodiments, the dilation system may include a trigger or other control mechanism integral with and on the handle 128 and that is can be selectively operated to inflate and deflate the balloon 174, 374. In some embodiments, an inflation mechanism (e.g., a pump or syringe) and/or an inflation fluid reservoir are integrated into the handle 128.

According to further embodiments, the delivery system may include a trigger or other control mechanism integral with and on the handle 128 and that is can be selectively operated to control delivery of fluid (e.g., irrigation fluid and/or medication) through the delivery lumen 144, 367. In some embodiments, an transfer mechanism (e.g., a pump or syringe) and/or a fluid reservoir (e.g., containing irrigation fluid and/or medication) are integrated into the handle 128.

In some embodiments, the instruments 120, 320 may include one or more interchangeable or replaceable modular components. For example, the instrument 120 can be configured such that the probe 130 is releasably coupled to the base 122. After the instrument 120 has been used to conduct a procedure, the probe 130 can be removed and discarded, recycled, or cleaned and sterilized, for example. A new probe 130 can then be mounted on and coupled to the base 122 and the base 122 can be re-used with the new probe 130 to conduct another procedure. Thus, an instrument according to some embodiments (e.g., the instrument 120 or the instrument 320) may include a combination of re-usable and disposable components.

According to some embodiments, the balloon 174, 374 of each instrument 120, 320 is substantially non-compliant. That is, the ability of the balloon material to stretch beyond a prescribed expansion size as the pressure is increased and thereby further expand the size of the balloon is very small. The balloon may be pleated and wrapped onto the shaft 132, 332 in its un-inflated position to provide a small initial uninflated balloon profile. When the balloon is inflated, it will unwrap to an initial fully inflated balloon diameter. Then, over quite a small range of plastic deformation, the balloon can be further expanded with additional pressure (via the pressurized fluid). The nominal diameter (i.e., the nominal inflated balloon diameter measured at a specified pressure) of balloon may be set at a pressure between the pressure required to fully expand the pleats and unwrap the balloon and the pressure that would cause the balloon to burst ("rated burst pressure"). Relatively high balloon inflation pressures as described herein may be required to provide sufficient force against the sinus anatomy and, in particular, to push back tissues and break small bones in the sinuses.

In some embodiments, the balloon 174, 374 is inflated multiple times during a procedure on a patient to execute multiple dilation procedures as described herein. These multiple balloon dilations can be applied to the same anatomy or to different locations in the sinuses.

In some embodiments, the instrument 120, 320 is configured and used to deliver a medication (e.g., a drug formulation in solution, suspension or emulsion) through the balloon 174, 374. In this case, the medication may be included in the inflation fluid. When the balloon is pressurized and inflated, a portion of the inflation fluid will seep or weep out of the balloon (e.g., through small pores) and onto the surrounding anatomy. In this case, a portion of the balloon wall may be formed of a microporous membrane through which the medication passes.

Aspects of some embodiments include:

Aspect 1. A device for dilating the paranasal sinus ostia and sinus outflow pathways comprising: a rigid and yet malleable guide member having a proximal end and a distal end; a guide member coupled to a balloon on its outer surface, lumen of the guide member having nested tubes for suction/aspiration, fluid or medicament delivery, and a fiber optic connected to a light source and a handle in the shape of a handle of a handgun disposed along a proximal portion of the guide member, the handle containing a housing for the light source and interface of the light source to the fiber optic wire, a closed fluid transit system that distally ends at the proximal end of the guide member and proximally ends in 3 separate tubing that can be independently and simultaneously operated without the action of one affecting the other.

Aspect 2. The device of Aspect 1, wherein the rigid guide member comprises a lumen along a length thereof.

Aspect 3. The device of Aspect 2, further comprising a system of nested tubes within the length of the lumen of the rigid guide member. The nested tubes carry out independent and simultaneous functions of suction/aspiration, fluid or medicament delivery and proving a passage for the fiber optic light wire carrying light from the light source housed in the handle of the device of claim 1 and ending distally at the distal tip of the rigid guide member.

Aspect 4. The device of Aspect 1, wherein the distal end of the substantially rigid guide member is malleable enough to be bent in various angles and shapes depending upon the anatomy and operator preference.

Aspect 5. The device of claim Aspect 4, wherein a distal end of the rigid member ends with a hollow bulbous tip to not only allow for atraumatic procedure but also allow for the independent and simultaneous functions of suction/aspiration, fluid or medicament delivery as desired by the operator.

Aspect 8. The device of Aspect 1, wherein the inflating lumen of the balloon is coupled on the surface of the guide member.

Aspect 9. The device of Aspect 1, wherein the inflating lumen of the balloon is fluidically connected to the inside of the balloon at its distal end and proximally connected to the inflation port.

Many alterations and modifications may be made by those having ordinary skill in the art, given the benefit of present disclosure, without departing from the spirit and scope of the invention. Therefore, it must be understood that the illustrated embodiments have been set forth only for the purposes of example, and that it should not be taken as limiting the invention as defined by the following claims. The following claims, therefore, are to be read to include not only the combination of elements which are literally set forth but all equivalent elements for performing substantially the same function in substantially the same way to obtain substantially the same result. The claims are thus to be understood to include what is specifically illustrated and described above, what is conceptually equivalent, and also what incorporates the essential idea of the invention.

What is claimed is:

1. An instrument system for treating a sinus of a subject, the instrument system comprising:
   an instrument including:
      a base configured to be gripped by an operator;
      an elongate probe including a probe proximal end coupled with the base and extending to a probe distal end, the probe including:
         an aspiration lumen terminating at an inlet port proximate the probe distal end; and
         a delivery lumen terminating at an outlet port proximate the probe distal end;
      a dilation balloon mounted on and surrounding a portion of the probe proximate the probe distal end, wherein the dilation balloon is expandable into an expanded configuration to execute a dilation operation; and
      a waveguide on the probe and having a light emitting end proximate the probe distal end;
   wherein:
      the instrument includes an integral aspiration controller operable to selectively control fluid flow between a suction source and the aspiration lumen,
   wherein the integral aspiration controller is mounted on the base;
      the probe defines a probe longitudinal axis from the probe proximal end to the probe distal end;
      the base includes a handle configured to be gripped by a hand of the operator;
      the handle has a handle axis extending at a transverse angle to the probe longitudinal axis; and
      the integral aspiration controller includes a trigger mounted on the base and operable by the operator's hand while gripping the handle to selectively control fluid flow between the suction source and the aspiration lumen.

2. The instrument system of claim 1 wherein:
the probe includes a rigid, elongate shaft;
the aspiration lumen and the delivery lumen extend through the shaft;
the dilation balloon is mounted on and surrounds a portion of a distal end portion of the shaft; and
a distal end portion of the waveguide extends longitudinally along the shaft and radially between the dilation balloon and an outer surface of the shaft.

3. The instrument system of claim 1 wherein:
the probe includes a rigid, elongate shaft;
the aspiration lumen is defined in the shaft;
the instrument includes a delivery conduit extending through the aspiration lumen; and
the delivery lumen is defined in the delivery conduit.

4. The instrument system of claim 1 wherein:
the probe includes a rigid, elongate shaft;
the aspiration lumen and the delivery lumen extend through the shaft; and
the shaft is malleable.

5. The instrument system of claim 1 wherein the instrument includes an integral lighting system including:
the waveguide;
a light source; and
a battery to power the light source;
wherein the integral lighting system is configured to transmit light through the waveguide from the light source to the light emitting end.

6. The instrument system of claim 5 wherein the light source and the battery are mounted in the base.

7. The instrument system of claim 6 wherein the light source and the battery are mounted in the handle.

8. The instrument system of claim 5 wherein the light source includes a light emitting diode (LED).

9. The instrument system of claim 1 further including an endoscope.

10. The instrument system of claim 1 including:
the suction source, wherein the suction source is fluidly connected to the aspiration lumen and operable to generate a negative pressure in the aspiration lumen to execute an aspiration operation wherein the instrument system draws material into the aspiration lumen through the inlet port; and
an irrigation fluid source fluidly connected to the delivery lumen and operable to execute a fluid delivery operation wherein the instrument system flows a fluid through the delivery lumen and out through the outlet port.

11. The instrument system of claim 10 wherein:
the instrument system includes a delivery controller operable to selectively control fluid flow between the irrigation fluid source and the delivery lumen; and
the aspiration controller and the delivery controller are operable by the operator to execute the aspiration operation and the fluid delivery operation simultaneously.

12. The instrument system of claim 11 wherein:
the instrument system includes a dilation controller operable to selectively inflate and deflate the dilation balloon; and
the aspiration controller and the delivery controller are operable by the operator to execute the aspiration operation and the fluid delivery operation simultaneously while the dilation balloon is in its expanded configuration.

13. The instrument system of claim 1 wherein the handle axis is substantially perpendicular to the probe longitudinal axis.

14. The instrument system of claim 1 wherein:
the probe includes a rigid, elongate shaft;
the dilation balloon is mounted on and surrounds a portion of a distal end portion of the shaft;
a distal end portion of the waveguide extends longitudinally along the shaft and radially between the dilation balloon and an outer surface of the shaft;
the aspiration lumen is defined in the shaft;
the instrument includes a delivery conduit extending through the aspiration lumen;
the delivery lumen is defined in the delivery conduit;
the shaft is malleable; and
the instrument includes an integral lighting system including:
the waveguide;
a light source; and
a battery to power the light source;
wherein the integral lighting system is configured to transmit light through the waveguide from the light source to the light emitting end; and
the light source and the battery are mounted in the handle.

15. A method for treating a sinus of a subject, the method comprising:
providing an instrument including:
a base configured to be gripped by an operator;
an elongate probe including a probe proximal end coupled with the base and extending to a probe distal end, the probe including:
an aspiration lumen terminating at an inlet port proximate the probe distal end; and
a delivery lumen terminating at an outlet port proximate the probe distal end;
a dilation balloon mounted on and surrounding a portion of the probe proximate the probe distal end, wherein the dilation balloon is expandable into an expanded configuration to execute a dilation operation; and
a waveguide on the probe and having a light emitting end proximate the probe distal end;
wherein:
the instrument includes an integral aspiration controller operable to selectively control fluid flow between a suction source and the aspiration lumen,
wherein the integral aspiration controller is mounted on the base;
the probe defines a probe longitudinal axis from the probe proximal end to the probe distal end;
the base includes a handle configured to be gripped by a hand of the operator;
the handle has a handle axis extending at a transverse angle to the probe longitudinal axis; and
the integral aspiration controller includes a trigger mounted on the base and operable by the operator's hand while gripping the handle to selectively control fluid flow between the suction source and the aspiration lumen;
operating the trigger to execute an aspiration operation wherein the instrument system draws material into the aspiration lumen through the inlet port;

executing a fluid delivery operation wherein the instrument system flows a fluid through the delivery lumen and out through the outlet port; and executing an illumination operation wherein the instrument system transmits light through the waveguide and out through the light emitting end.

16. An instrument system for treating a sinus of a subject, the instrument system comprising:
    an instrument including:
        a base configured to be gripped by an operator;
        an elongate probe including a probe proximal end coupled with the base and extending to a probe distal end, the probe including:
            an aspiration lumen terminating at an inlet port proximate the probe distal end; and
            a delivery lumen terminating at an outlet port proximate the probe distal end;
        a dilation balloon mounted on the probe proximate the probe distal end,
    wherein the dilation balloon is expandable into an expanded configuration to execute a dilation operation; and
        a waveguide on the probe and having a light emitting end proximate the probe distal end;
    wherein:
        the probe includes a rigid, elongate shaft;
        the aspiration lumen and the delivery lumen extend through the shaft;
        the dilation balloon is mounted on and surrounds a portion of a distal end portion of the shaft; and
        a distal end portion of the waveguide extends longitudinally along the shaft and radially between the dilation balloon and an outer surface of the shaft.

17. The instrument system of claim 16 wherein:
the aspiration lumen is defined in the shaft;
the instrument includes a delivery conduit extending through the aspiration lumen; and
the delivery lumen is defined in the delivery conduit.

18. The instrument system of claim 16 wherein the shaft is malleable.

19. An instrument system for treating a sinus of a subject, the instrument system comprising:
    an instrument including:
        a base configured to be gripped by an operator;
        an elongate probe including a probe proximal end coupled with the base and extending to a probe distal end, the probe including:
            an aspiration lumen terminating at an inlet port proximate the probe distal end; and
            a delivery lumen terminating at an outlet port proximate the probe distal end;
        a dilation balloon mounted on the probe proximate the probe distal end,
    wherein the dilation balloon is expandable into an expanded configuration to execute a dilation operation; and
        an integral lighting system including:
            a light source; and
            a battery to power the light source; and
            a waveguide on the probe and having a light emitting end proximate the probe distal end, wherein the integral lighting system is configured to transmit light through the waveguide from the light source to the light emitting end.

20. The instrument system of claim 19 wherein the light source and the battery are mounted in the base.

21. The instrument system of claim 19 further including an endoscope.

* * * * *